(12) United States Patent
Andriacchi et al.

(10) Patent No.: US 10,307,256 B2
(45) Date of Patent: Jun. 4, 2019

(54) KNEE REPLACEMENT SYSTEM AND METHOD FOR ENABLING NATURAL KNEE MOVEMENT

(75) Inventors: Thomas P. Andriacchi, Los Altos Hills, CA (US); Jorge O. Galante, Sanibel, FL (US)

(73) Assignee: Biomet Manufacturing, LLC, Warsaw, IN (US)

( * ) Notice: Subject to any disclaimer, the term of this patent is extended or adjusted under 35 U.S.C. 154(b) by 1133 days.

(21) Appl. No.: 12/815,730

(22) Filed: Jun. 15, 2010

(65) Prior Publication Data

US 2011/0022179 A1 Jan. 27, 2011

Related U.S. Application Data

(60) Provisional application No. 61/307,070, filed on Feb. 23, 2010, provisional application No. 61/228,720, filed on Jul. 27, 2009.

(51) Int. Cl.
*A61F 2/38* (2006.01)
*A61F 2/46* (2006.01)
*A61F 2/30* (2006.01)

(52) U.S. Cl.
CPC .............. *A61F 2/3836* (2013.01); *A61F 2/38* (2013.01); *A61F 2/389* (2013.01); *A61F 2/3859* (2013.01);
(Continued)

(58) Field of Classification Search
CPC ........ A61F 2/38; A61F 2/3859; A61F 2/3877; A61F 2/389; A61F 2002/30616
(Continued)

(56) References Cited

U.S. PATENT DOCUMENTS 5,326,361 A * 7/1994 Hollister ............... 623/20.31
5,733,292 A 3/1998 Gustilo et al.
(Continued)

FOREIGN PATENT DOCUMENTS

CN 201175391 Y 1/2009
WO WO-2011016905 A1 2/2011

OTHER PUBLICATIONS

China First Office Action dated Mar. 31, 2014 for China Application No. 201080041370.X.
(Continued)

*Primary Examiner* — Brian E Pellegrino
(74) *Attorney, Agent, or Firm* — Schwegman Lundberg & Woessner, P.A.

(57) ABSTRACT

A knee replacement system, and a method for supplying and implanting a knee replacement system, for enabling natural knee movement in a leg in a patient, including: a medial femoral component having a medial femoral articulating surface with a sagittal plane profile including four medial femoral arcuate portions scaled by a first femoral scaling factor; a lateral femoral component having a lateral femoral articulating surface with a sagittal plane profile including four lateral femoral arcuate portions scaled by a second femoral scaling factor; a medial tibial component having a medial tibial articulating surface that articulates with the medial femoral articulating surface and includes a first raised medial edge that increases in width in an anterior direction; and a lateral tibial component having a lateral tibial articulating surface that articulates with the lateral femoral articulating surface and includes a second raised medial edge that increases in width in the anterior direction.

28 Claims, 15 Drawing Sheets

(52) U.S. Cl.
CPC .......... *A61F 2/3877* (2013.01); *A61F 2/4684* (2013.01); *A61F 2002/30574* (2013.01); *A61F 2002/30616* (2013.01); *A61F 2002/30754* (2013.01); *A61F 2002/3895* (2013.01); *A61F 2310/00023* (2013.01); *A61F 2310/00029* (2013.01); *A61F 2310/00059* (2013.01); *A61F 2310/00089* (2013.01); *A61F 2310/00101* (2013.01)

(58) Field of Classification Search
USPC ............... 623/20.15, 20.19, 20.21, 20.31
See application file for complete search history.

(56) References Cited

U.S. PATENT DOCUMENTS

| | | | |
|---|---|---|---|
| 5,879,390 | A | 3/1999 | Kubein-Meesenburg et al. |
| 6,152,960 | A | 11/2000 | Pappas |
| 6,482,209 | B1 | 11/2002 | Engh et al. |
| 6,540,787 | B2 | 4/2003 | Biegun et al. |
| 6,616,696 | B1 | 9/2003 | Merchant |
| 6,893,467 | B1* | 5/2005 | Bercovy ................ 623/20.14 |
| 7,326,252 | B2 | 2/2008 | Otto et al. |
| 7,338,524 | B2 | 3/2008 | Fell et al. |
| 7,387,644 | B2 | 6/2008 | Beynnon et al. |
| 9,314,342 | B2 | 4/2016 | Andriacchi et al. |
| 2002/0082607 | A1 | 6/2002 | Heldreth et al. |
| 2003/0187452 | A1 | 10/2003 | Smith et al. |
| 2003/0225458 | A1* | 12/2003 | Donkers et al. ........ 623/20.15 |
| 2004/0039398 | A1 | 2/2004 | Cortellessa et al. |
| 2004/0064191 | A1 | 4/2004 | Wasielewski |
| 2005/0107884 | A1 | 5/2005 | Johnson et al. |
| 2005/0177169 | A1 | 8/2005 | Fisher et al. |
| 2006/0058883 | A1 | 3/2006 | Aram et al. |
| 2006/0190086 | A1 | 8/2006 | Clemow et al. |
| 2007/0135926 | A1* | 6/2007 | Walker .................. 623/20.31 |
| 2007/0173946 | A1 | 7/2007 | Bonutti |
| 2008/0091209 | A1* | 4/2008 | Schmotzer et al. ........... 606/88 |
| 2008/0172125 | A1* | 7/2008 | Ek ........................... 623/14.12 |
| 2009/0043396 | A1 | 2/2009 | Komistek |
| 2009/0265011 | A1* | 10/2009 | Mandell ................ 623/20.15 |
| 2009/0319047 | A1* | 12/2009 | Walker .................. 623/20.15 |
| 2010/0016978 | A1 | 1/2010 | Williams et al. |
| 2010/0191341 | A1 | 7/2010 | Byrd |
| 2011/0251694 | A1 | 10/2011 | Wasielewski |
| 2013/0103159 | A1 | 4/2013 | Andriacchi et al. |

OTHER PUBLICATIONS

China Second Office Action dated Nov. 18, 2014 for China Application No. 201080041370.X.
"U.S. Appl. No. 13/716,331, Examiner Interview Summary dated Nov. 6, 2015", 3 pgs.
"U.S. Appl. No. 13/716,331, Non Final Office Action dated Aug. 28, 2015", 11 pgs.
"U.S. Appl. No. 13/716,331, Notice of Allowance dated Dec. 18, 2015", 5 pgs.
"U.S. Appl. No. 13/716,331, Response filed Jun. 2, 2015 to Restriction Requirement dated Apr. 2, 2015", 1.
"U.S. Appl. No. 13/716,331, Response filed Nov. 20, 2015 to Non Final Office Action dated Aug. 28, 2015", 12 pgs.
"U.S. Appl. No. 13/716,331, Restriction Requirement dated Apr. 2, 2015", 6 pgs.
"Chinese Application Serial No. 201080041370.X, Response filed Jul. 29, 2015 to Office Action dated May 11, 2015", (W/ English Translation), 8 pgs.
"International Application Serial No. PCT/US2010/038740, International Preliminary Report on Patentability dated Feb. 9, 2012", 10 pgs.
"International Application Serial No. PCT/US2010/038740, International Search Report dated Oct. 21, 2010", 3 pgs.
"International Application Serial No. PCT/US2010/038740, Invitation to Pay Additional Fees and Partial Search Report dated Aug. 5, 2010", 2 pgs.
"International Application Serial No. PCT/US2010/038740, Written Opinion dated Oct. 21, 2010", 8 pgs.

* cited by examiner

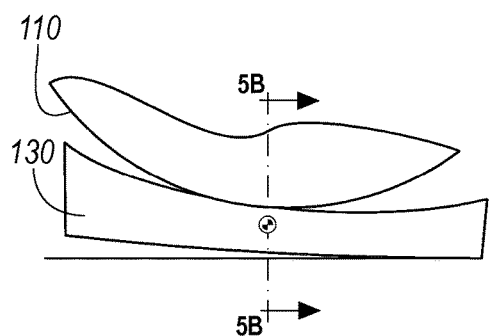 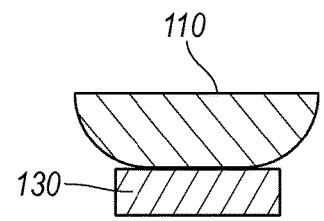
FIG. 5A  FIG. 5B
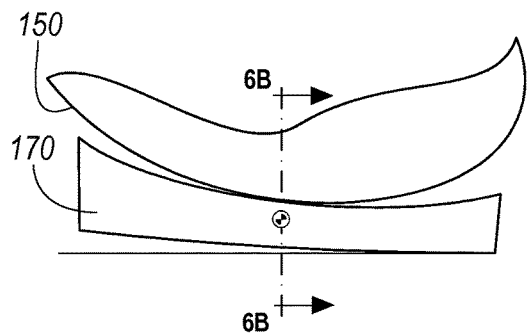 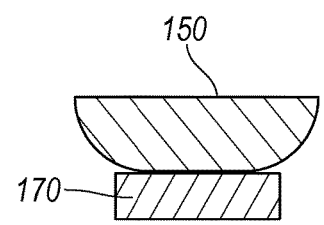
FIG. 6A  FIG. 6B

| EXAMPLE MODES (NON-COMPREHENSIVE) | | MEDIAL FEMORAL | MEDIAL TIBIAL | LATERAL FEMORAL | LAERAL TIBIAL | PATELLAR FLANGE | PATELLAR SURFACE REPLACEMENT | PATELLAR COMPONENT |
|---|---|---|---|---|---|---|---|---|
| 1 | | X | | | | | | |
| 2 | | | X | | | | | |
| 3 | | | | | | | | X |
| 4 | | | | X | X | | | |
| 5 | | | | | | X | X | |
| 6 | | | | | | X | X | |
| (PARTIAL FEMORAL COMPONET) | | X | | X | | X | | |
| (FULL FEMORAL COMPONENT) | | | | X | | X | | |
| (TOTAL KNEE REPLACEMENT) | | X | X | X | X | X | | X |

X = USED IN MODE

FIG. 13

KNEE REPLACEMENT SYSTEM AND METHOD FOR ENABLING NATURAL KNEE MOVEMENT

CROSS-REFERENCE TO RELATED APPLICATIONS

This application claims the benefit of U.S. Provisional Applications Nos. 61/228,720 filed 27 Jul. 2009 and 61/307,070 filed 23 Feb. 2010, which are both incorporated in their entirety by this reference.

TECHNICAL FIELD

This invention relates generally to the knee arthroplasty field, and more specifically to an improved knee replacement system for enabling natural knee movement over a broad range of activities in the knee replacement field.

BACKGROUND

Knee arthroplasty, in which the knee is partially or completely replaced with a prosthetic knee, is a common surgical procedure performed to relieve pain or disability due to conditions such as osteoarthritis, rheumatoid arthritis and other forms of polyarthritis, cartilage defects, meniscus tears, and ligament tears. Knee arthroplasty typically replaces diseased or damaged joint surfaces of the knee, including surfaces on the femur, tibia and/or patella with artificial replacement components made of metal or plastic parts designed to allow for knee motion that is natural as possible. Natural knee motion is the result of a complex relationship between primary movements of flexion-extension and secondary movements of anterior-posterior translation and internal-external rotation. This complex relationship defines a functional envelope of motion, which varies from activity to activity.

Current knee replacement systems are unable to facilitate natural functional envelopes of motion, fail to engage the anterior and posterior cruciate ligaments and are therefore less-than-ideal for enabling natural knee movement over a wide range of activities of daily living. Current knee replacement systems also typically limit the activities of patients with knee replacements, and do not address the high performance needs and desires of younger or more active aging patients who typically participate in higher impact activities such as running.

Thus, there is a need in the knee replacement field to create an improved knee replacement system that facilitates natural knee movement over a broad range of activities. This invention provides such an improved knee replacement system.

BRIEF DESCRIPTION OF THE FIGURES

FIGS. 5A and 5B are a sagittal view and frontal cross section view, respectively, of an example articulation between the medial femoral component and the medial tibial component of the preferred embodiment;

FIGS. 6A and 6B are a sagittal view and frontal cross section view, respectively, of an example articulation between the lateral femoral component and the lateral tibial component of the preferred embodiment;

FIG. 13 is a table schematically illustrating several example modes in which a selected portion of the components of the system of the preferred embodiment may be implanted;

DESCRIPTION OF THE PREFERRED EMBODIMENTS

The following description of preferred embodiments of the invention is not intended to limit the invention to these preferred embodiments, but rather to enable any person skilled in the art to make and use this invention. In the following description, unless otherwise stated, the terms "proximal", "distal", "medial" and "lateral" are used relative to the midline of a person.

1. Knee Replacement System for Enabling Natural Knee Movement

Figure 1:
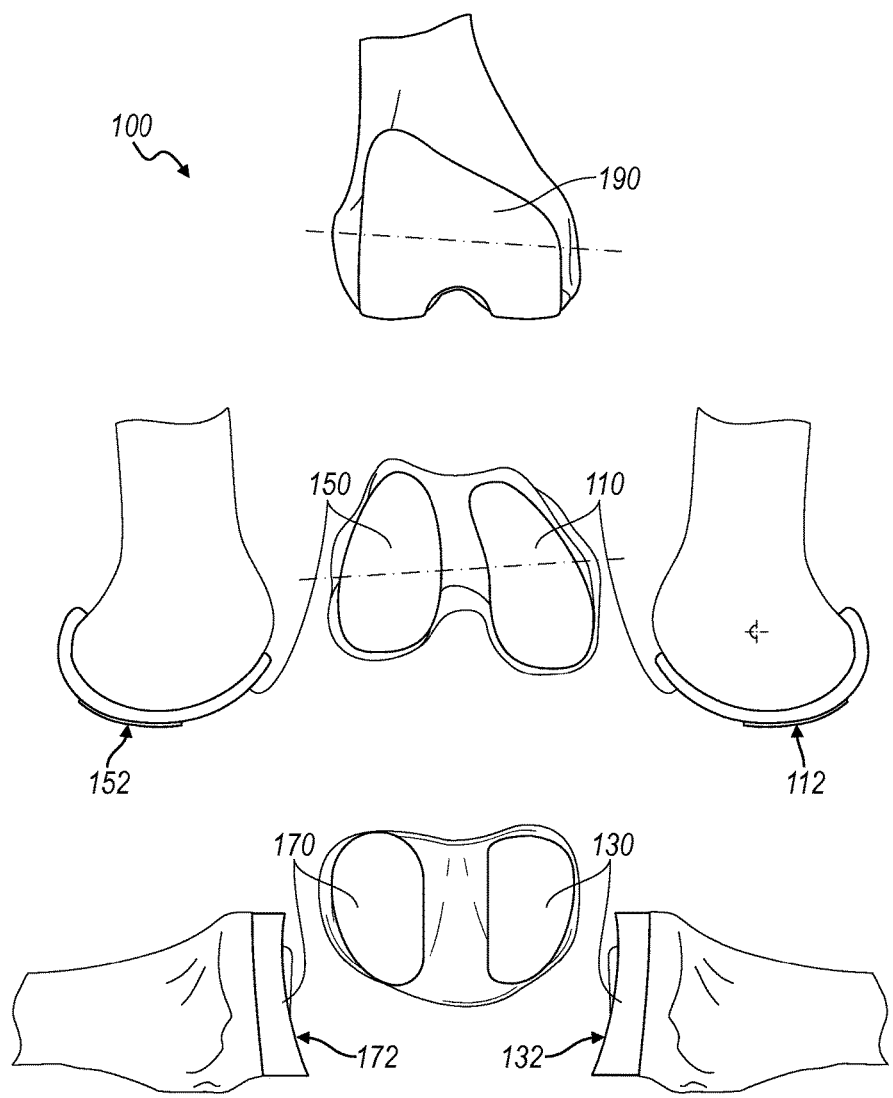
FIG. 1 is a schematic unfolded view of the preferred embodiment of the knee replacement system.

As shown in FIG. 1, the knee replacement system 100 preferably includes a medial femoral component 110, a medial tibial component 130, a lateral femoral component 150, a lateral tibial component 170, and a patellar flange component 190. The knee replacement system 100 may further include a patellar component. In an alternative embodiment, the medial femoral component 110, lateral femoral component 150, and/or patellar flange component 190 may be integrated into a full femoral component or a partial femoral component of unitary construction. Similarly, in another alternative embodiment, the medial tibial component 130 and lateral tibial component 170 may be integrated into a full tibial component of unitary construction. As shown in FIG. 13, the knee replacement system 100 is preferably modular and may be used in multiple modes, such that a selected portion or all of the components may be implanted in any combination in a patient, depending on the needs of the patient. In one example of a mode, only the medial femoral component 110 and the medial tibial component 130 may be implanted in a patient who has degradation in only the medial compartment of their knee. In another example of a mode, all components may be implanted in a patient who requires a total knee replacement. Furthermore, modular components allow any individual component to be customized for a patient if needed, without requiring the entire system to be customized.

Figure 2:
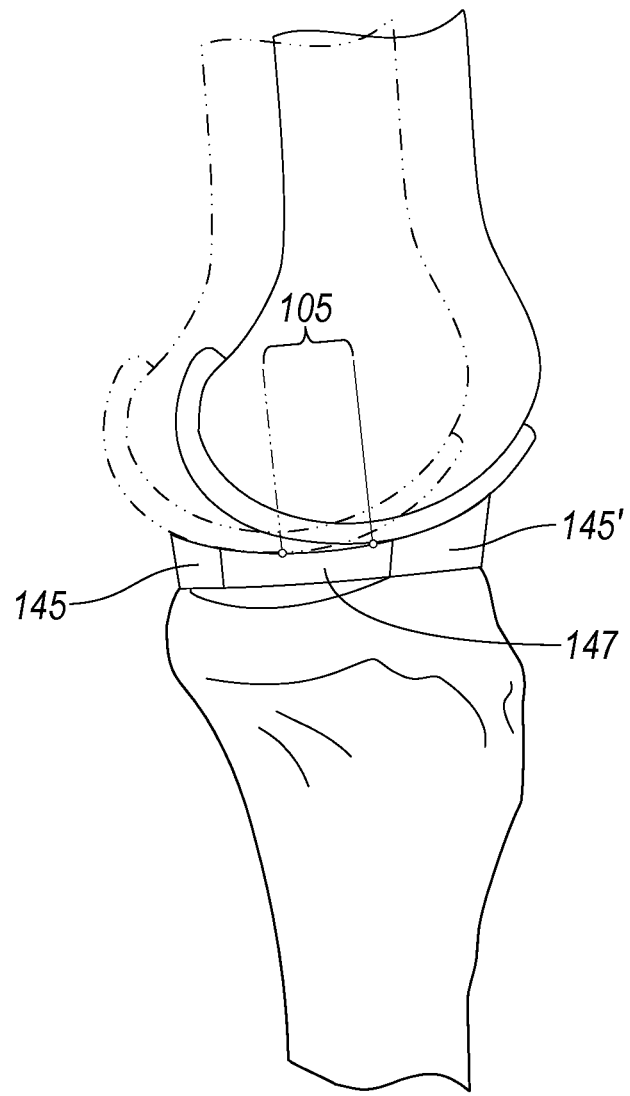
FIG. 2 is a side view of a femoral component articulating with a tibial component of the preferred embodiment.
Figure 3A:
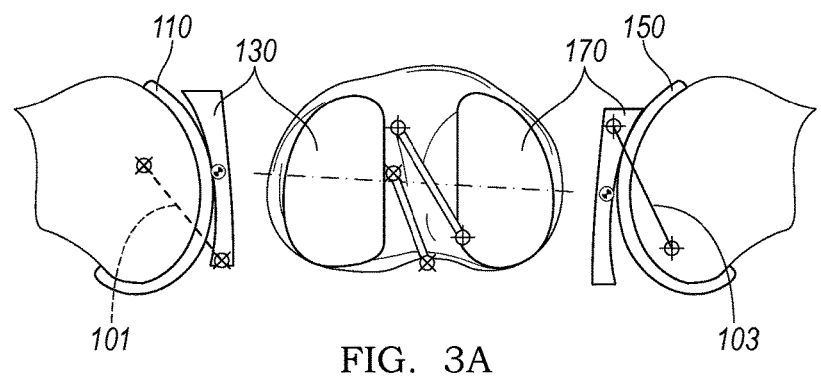
FIGS. 3A, 3B, and 3C are unfolded views of the medial tibial component and the lateral tibial component of the preferred embodiment in neutral stance, heel strike phase, and toe off phase, respectively.
Figure 3B:
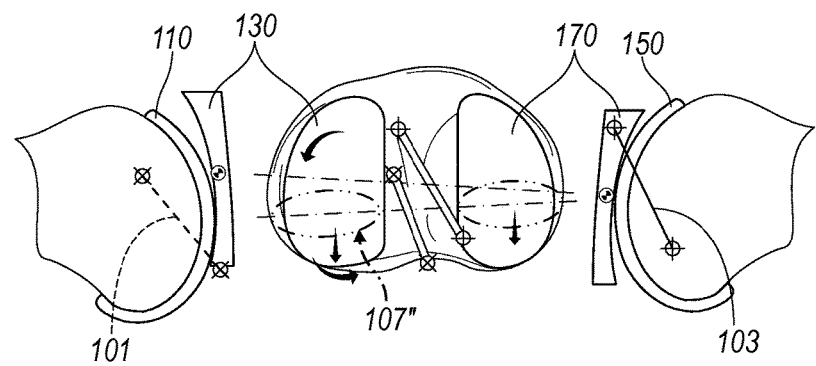
Figure 3C:
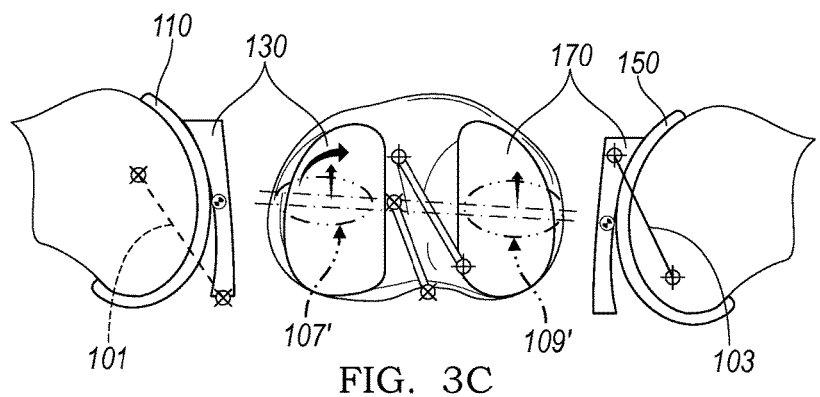
Figure 4A:
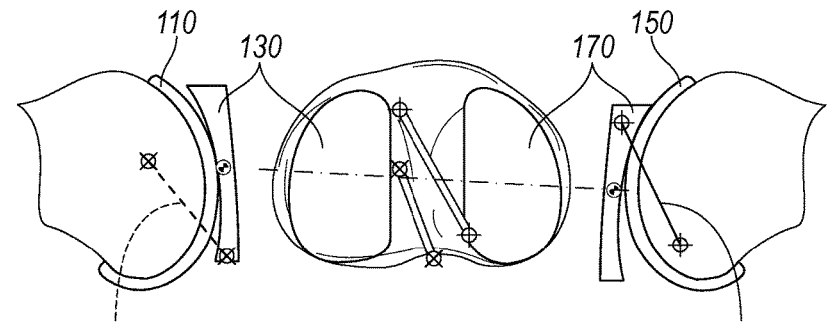
FIGS. 4A, 4B, and 4C are unfolded views of the medial tibial component and the lateral tibial component of the preferred embodiment in neutral stance, flexion during stair climbing, and deep flexion, respectively.
Figure 4B:
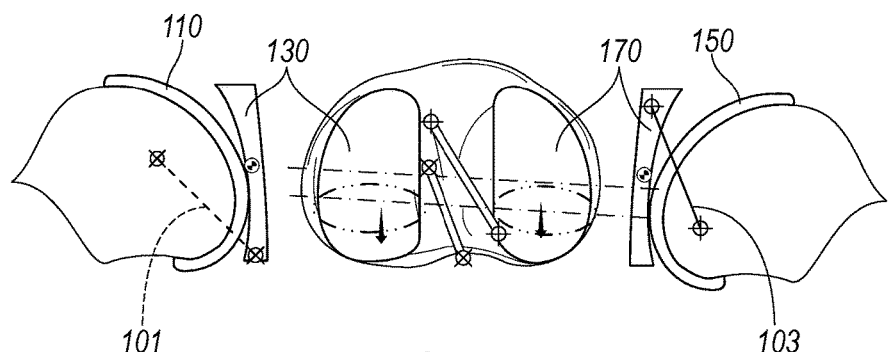

The knee replacement system 100 preferably enables a range of knee motion having the following characteristics: (1) Hyperextension of up to approximately −15 to −20 degrees; (2) At full extension (leg angle of 0 degrees), the leg may undergo external rotation of approximately 10 to 15 degrees and internal rotation of approximately 10 to 15 degrees; (3) At moderate flexion (leg angle of approximately 20 to 30 degrees), the leg may undergo external rotation of up to approximately 15 degrees and internal rotation of up to −15 degrees; (4) At higher flexion (leg angle of 120 degrees or more), the leg may undergo external rotation of between approximately 25 and 30 degrees with posterior translation of the lateral tibial component; and (5) Deep flexion of up to approximately 145 degrees. The knee replacement system 100 is designed to enable natural knee motion by facilitating natural envelopes of functional motion (EFMs), such as the EFM 105 shown in FIG. 2, that describe possible ranges of translational motions between the articulating surfaces of the femur and the tibia over a broad range of activities, and by allowing motion between medial components to be different from lateral components. As shown in FIGS. 3 and 4, natural EFMs include a medial EFM 107 defined between an anterior range 107' and a posterior range 107", and a lateral EFM 109 defined between an anterior range 109' and a posterior range 109". The medial EFM 107 is the range of movement at the articular surface between the medial sides of the femur and tibia. Similarly, the lateral EFM 109 is the range of movement at the articular surface between the lateral sides of the femur and tibia. The knee replacement system 100 preferably facilitates natural EFMs by permitting a range of movement, including different medial side and lateral side component motion, at the articular surface between the femur and the tibia of the knee joint when the knee flexes at particular key flexion angles. The EFMs provided by the knee replacement system 100 preferably change as the knee flexes at these key flexion angles. The knee replacement system preferably further facilitates natural EFMs by incorporating the anterior and posterior cruciate ligaments, which are preferably tensioned at specified knee flexion angles during implantation of the knee replacement system.

In one embodiment, the knee replacement system 100 preferably defines a medial EFM 107 based on the amount of anterior-posterior translation and internal-external rotation that the knee undergoes during walking, stair-climbing and deep flexion as a function of knee flexion angle. The EFMs based on these activities preferably also cover the range of EFMs for a broader range of daily activities such as running or rising from a chair. As an example, as shown in FIG. 3, the anterior range 107' and posterior range 107" of the medial EFM for walking are a result of the relative positions of the articulating surfaces of the medial femoral component 110 and the medial tibial component 130 during the toe off and heel strike phases, respectively, of the walking gait cycle. The range of movement that naturally occurs when the knee is sustaining high compressive loads, such as during walking, squatting and other activities may further define the medial EFM.

Figure 4C:
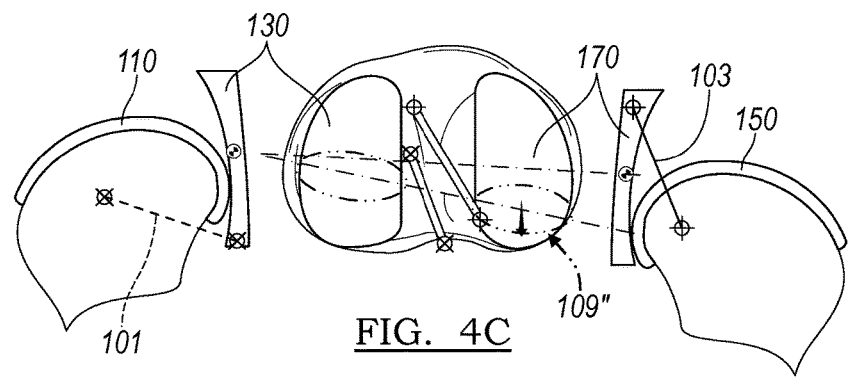

Similar to the medial EFM 107, the knee replacement system preferably defines a lateral EFM 109 based on the amount of internal and external rotation that the knee undergoes during walking and deep flexion as a function of knee flexion angle. As an example, as shown in FIG. 3C, the anterior range 109' of the lateral EFM for walking is a result of the relative positions of the articulating surfaces of lateral femoral component 150 and the lateral tibial component 170 during the toe off phase of the walking gait cycle. As shown in FIG. 4C, the posterior range of the lateral EFM for walking is a result of the relative positions of the lateral femoral component 150 and the lateral tibial component 170 during activities involving deep flexion, such as stair climbing and squatting. The range of movement that naturally occurs when the knee is sustaining high compressive loads, such as during walking, squatting and other activities, may further define the lateral EFM. The medial EFM 107 and lateral EFM 109 are preferably different from each other to allow uncoupled medial component and lateral component motions, which better emulates natural EFMs.

Figure 12A:
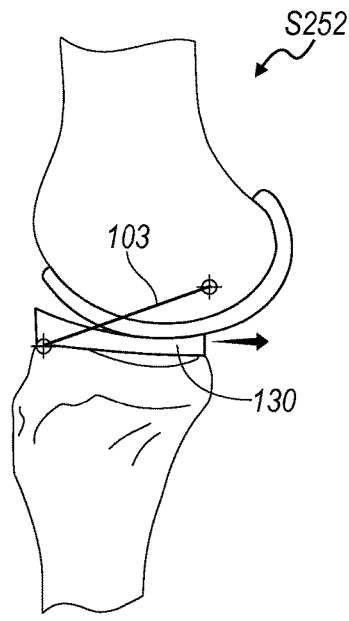
FIGS. 12A, 12B, and 12C are schematics of the steps of adjusting the posterior position of the medial tibial component, adjusting the anterior restraint of the lateral and medial tibial components, and adjusting the posterior position of the lateral tibial component, respectively, of the preferred embodiment.
Figure 12B:
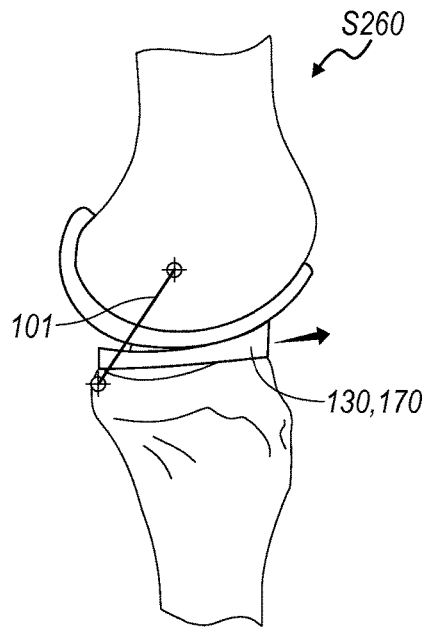
Figure 12C:
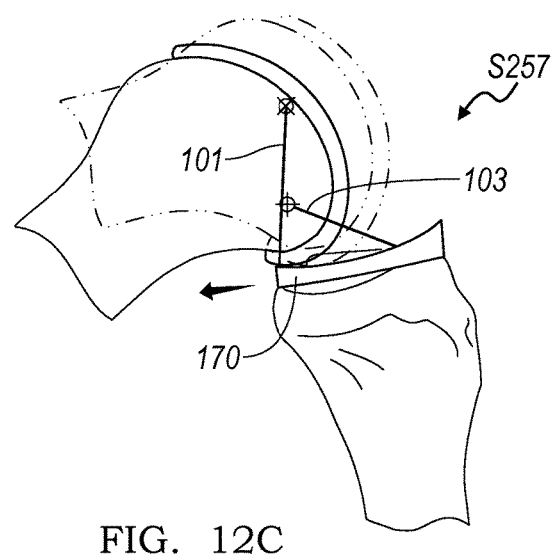

The medial and lateral EFMs are preferably further based on the incorporation of the cruciate ligaments. As one ordinarily skilled in the art will recognize, the anterior cruciate ligament (ACL) 103 and the posterior cruciate ligament (PCL) 101 normally function together to provide mobility and stability within the conditions defined by the medial and lateral EFMs. The anterior and posterior ranges of the EFMs are preferably adjusted such that the anterior and posterior constraints to motion are provided by the ACL 103 and PCL 101, and not the physical constraints of the articular surfaces of the femoral and tibial components. The posterior constraint of the medial EFM is preferably determined with the knee at full extension and the tibia anteriorly displaced and externally rotated, as shown in FIG. 12A. The anterior ranges of the medial and the lateral EFMs are preferably determined with the knee at full extension and the tibia posteriorly displaced and internally rotated, as shown in FIG. 12B. The posterior constraint of the lateral EFM is preferably determined with the knee in deep flexion and the tibia internally rotated, as shown in FIG. 12C.

Figure 7A:
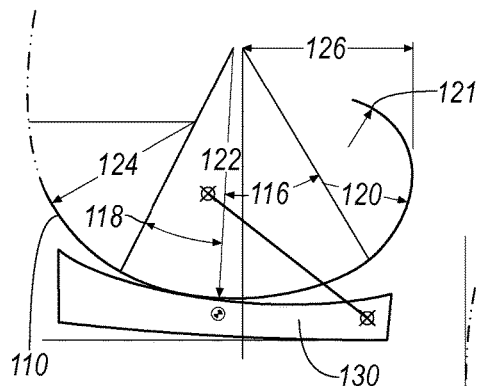
FIGS. 7A and 7B are sagittal views of the medial femoral component articulating with the medial tibial component and of the lateral femoral component articulating with the lateral tibial component, respectively, in the preferred embodiment.
Figure 10A:
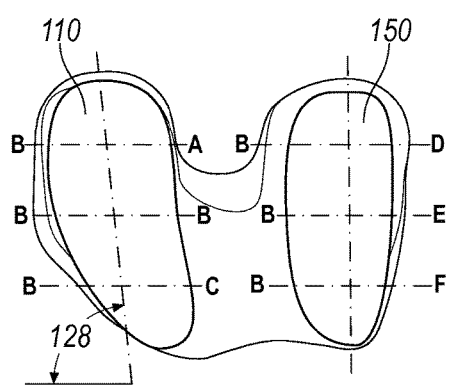
FIG. 10A is an inferior view schematic of the medial and lateral femoral components of the preferred embodiment implanted on a femur, with selected frontal cross sections of the medial and lateral femoral components.
Figure 10B:
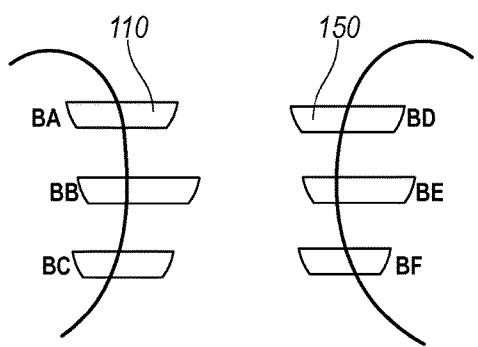
FIG. 10B is a view of frontal cross-sections of the medial and lateral femoral components, taken along the lines B-A through B-F of FIG. 10A.
Figure 11A:
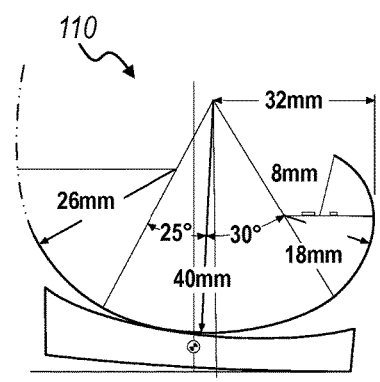
FIGS. 11A and 11B are sagittal views of example embodiments of the medial and lateral femoral components, respectively.
Figure 11B:
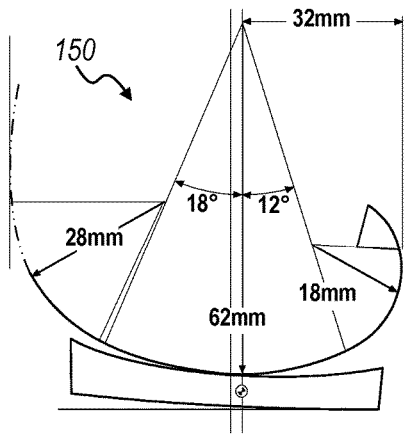
Figure 11C:
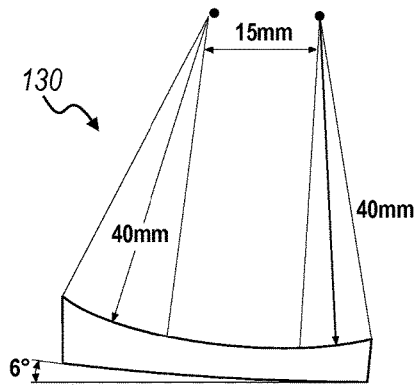
FIGS. 11C and 11D are frontal cross-section views of example embodiments of the medial and lateral femoral components, respectively.
Figure 11D:
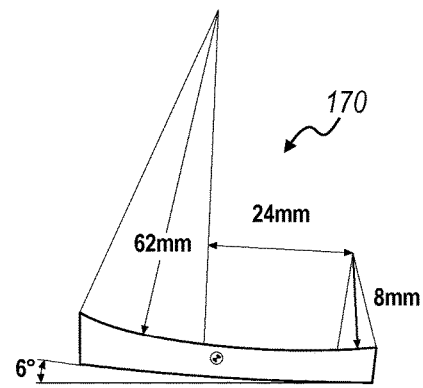
Figure 11E:
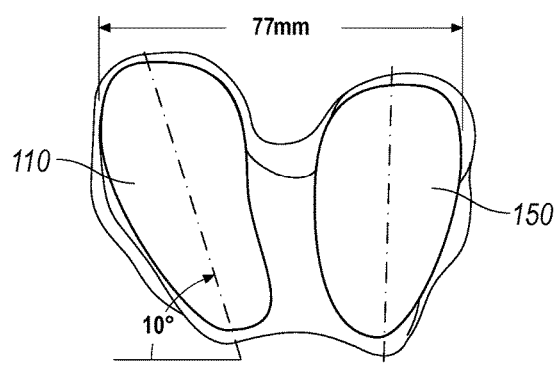
FIG. 11E is an inferior view of example embodiments of the medial and lateral femoral components, implanted on the medial and lateral condyles, respectively, of a femur.

The medial femoral component 110 of the knee replacement system functions to provide a bearing surface on the medial condyle of the femur. As shown in FIG. 1, the medial femoral component no is preferably implantable on the medial condyle on the distal end of the femur, and preferably includes a medial femoral articulating surface 112 that articulates with the medial tibial articulating surface 132 of the medial tibial component 130 throughout knee movement. As shown in FIGS. 1 and 10A, the medial femoral component no preferably covers and integrates with the medial condyle, and preferably includes an internal curvature to conform to the natural surface of the medial condyle. However, the medial femoral component no may alternatively have any suitable shape to conform to any suitable surface, including a condyle surface that is surgically manipulated to mate with the medial femoral component no. The frontal plane profile of the medial femoral articulating surface 112 preferably includes a blended radius, which may help reduce stress concentrations. The medial femoral component 110 is preferably one of a size selected from a group of available sizes, but may alternatively be a customized size and/or include customized features for a patient. As shown in FIG. 5B, the articulating surface of the medial femoral component 110 preferably includes a broad exterior curvature in the frontal plane, which minimizes contact stress by distributing force across the broad contact surface and permits sliding and rotation between the articulating surface. The radius of curvature of the medial femoral component no at the articulating points of contact with the medial tibial component 130 preferably varies with leg flexion angle, such that a specified range of articular motion occurs at key flexion angles. For example, the radius of curvature in the medial femoral component at the articulating point of contact between the medial femoral and medial tibial components for near full extension during walking is different than that for 45 degrees of flexion during stair climbing. As shown in FIG. 7A, the sagittal profile of the medial femoral articulating surface of the medial femoral component 110 is preferably defined by four medial femoral arcuate portions (a superior, a posterior, a distal, and an anterior medial femoral arcuate portions) and a scaling factor 126 measuring the offset from the posterior edge of the medial condyle in the central sagittal plane of the medial femoral component 110. The superior, posterior, distal, and anterior arcuate portions preferably have medial radii of curvature of a superior radius 121, posterior radius 120, a distal radius 122, and an anterior radius 124, respectively. The medial radii of curvature preferably originate from distinct arc centers, but may alternatively originate from any suitable points in the sagittal plane profile of the medial femoral component 110. The medial femoral arcuate portions are preferably designed based on anatomical measurements needed to provide the medial and lateral EFMs. As shown in FIG. 7A, the distal medial femoral arcuate portion preferably sweeps a greater angle than each of the posterior and anterior medial femoral arcuate portions, and preferably sweeps the sum of a posterior angle 116 and an anterior angle 118. The distal radius of curvature 122 is preferably longer than the posterior and anterior radii of curvature 120 and 124, respectively, and the relative lengths of the four medial radii of curvature 121, 120, 122 and 124 are preferably constant over the group of available sizes of the medial femoral component 110. Each of the group of available sizes of medial femoral components is preferably sized to the scaling factor 126. However, the medial femoral component may alternatively have any exterior shape that is suitable for articulating with the medial tibial component or natural tibial plateau. As shown in FIG. 10A, a central line (defined as the line extending from the midline of the posterior edge of the component 110 along the midline of the component width) in an inferior view of the component is preferably at an angle 128, and the exact angle measurement may depend on anatomy of the patient.

The medial femoral component 110 is preferably made of a biocompatible metal, such as zirconium, titanium, chromium, cobalt, molybdenum, and/or any suitable material, using milling, casting, sanding, polishing and/or other suitable manufacturing and finishing processes. The medial femoral component 110 is preferably implanted on the surface of the medial femoral condyle of a patient using biological fixation, other fixatives such as bone cement, or through any suitable method known and used by one skilled in the art, such as that described in U.S. Pat. No. 5,171,244, entitled, "Methods and apparatus for arthroscopic prosthetic knee replacement", which is incorporated in its entirety by this reference. Prior to implantation, the medial condyle may be prepared with a sequence of cuts, including a distal cut preferably perpendicular to the neutral axis of the femur, anterior and posterior cuts, and chamfer cuts to complement the internal curvature or surface of the medial femoral component no. These cuts may be made with the aid of jigs, instrumented tools, robotics or other devices to improve the accuracy of the cuts, and to improve the consistency of the interdependence between components of the knee replacement system. These materials and processes of manufacture and implantation are known and used in the art of knee replacement systems and other implanted devices, and their implementation would be readily understood by one ordinarily skilled in the art of knee replacement systems.

Figure 8A:
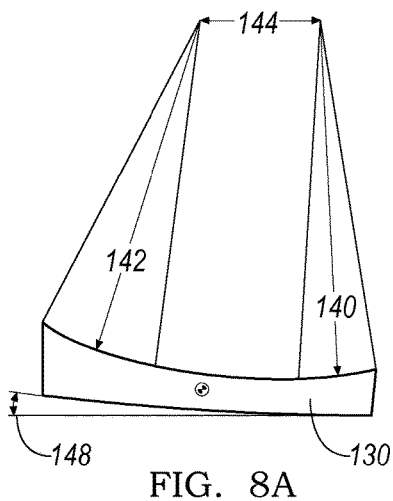
FIGS. 8A and 8B are sagittal view schematics of the medial functional envelope of motion and the lateral functional envelope of motion.
Figure 9A:
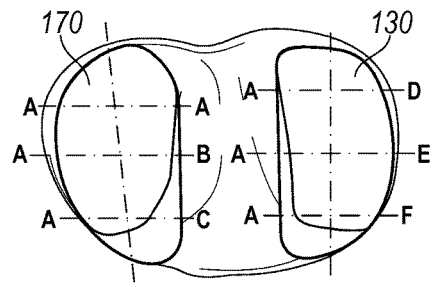
FIG. 9A is a superior view schematic of the medial and lateral tibial components of the preferred embodiment implanted on a tibia.

The medial tibial component 130 of the knee replacement system functions to provide a bearing surface on the medial tibial plateau of the tibia. As shown in FIGS. 1 and 9A, the medial tibial component 130 is implantable on the medial tibial plateau of the proximal end of the tibia and includes a medial tibial articulating surface 132 that preferably articulates with the medial femoral articulating surface 112 of the medial femoral component no throughout knee movement. The medial tibial component 130 preferably is implanted on the proximal end of the tibia, by attaching to a medial base plate that is fixated to a surgically-prepared proximal tibial plateau surface with biological fixation, bone cement, or another suitable fixative. However, the medial tibial component may alternatively be implanted directly to a surgically-prepared medial tibial plateau surface, similar to the medial femoral component no. Prior to implantation of the medial tibial component, the medial tibial plateau is preferably prepared with a sequence of cuts including a distal cut preferably perpendicular to the neutral axis of the tibia, and medial and lateral cuts having equal posterior slopes to facilitate proper function of the PCL and ACL. These cuts may be performed with a jig, instrumented tools, robotics or other devices to improve accuracy of the desired cuts and to improve the consistency of the interdependence between components of the knee replacement system. Where both the medial and lateral tibial components are implanted, the intercondylar eminence space between the medial and lateral tibial plateaus is preferably equal to or narrower than the width of the spacing between the medial and lateral femoral condyles, to facilitate proper articulation between the femur and tibia. The medial tibial component 130 is preferably implanted such that the bottom surface (the distal surface) is at an angle 148 relative to the horizontal. The exact measurement of angle 148 preferably depends on the anatomy of the patient. The angle 148 is preferably introduced by implanting the medial tibial component 130 in a sloped cut, but may alternatively be built into the medial tibial component 130 to allow a horizontal, neutral cut. As shown in FIGS. 8A and 9A, the medial tibial articulating surface 132 preferably includes a broad, nearly flat plateau surface in the sagittal and frontal planes that articulates with the medial femoral articulating surface 112 of the medial femoral component no. Like that of the medial femoral component, the articulating surface 132 of the medial tibial component 130 preferably minimizes contact stress by distributing force across the broad contact surface and minimizes rotational restraint. Furthermore, similar to the medial femoral component no, the radius of curvature of the medial tibial component 130 at the articulating points of contact between the medial tibial and the medial femoral components preferably varies with leg flexion angle, such that a specified range of articular motion occurs at key flexion angles. The medial tibial component 130 preferably includes a thickness and tibial plane coverage size that are selected from a group of available thicknesses and sizes based on the specific needs of the patient. For example, a petite patient may require a thinner and/or smaller planar sized medial tibial component than a larger patient. As shown in FIG. 8A, the sagittal profile of the medial tibial component 130 is preferably defined by two medial tibial arcuate portions (a posterior and an anterior medial tibial arcuate portions) and a scaling factor 144 measuring the medial EFM. The posterior and anterior medial tibial arcuate portions preferably have medial radii of 140 and 142, respectively. The medial tibial arcuate portions are preferably designed with considerations similar to those for the sagittal profile of the medial femoral component no, but for various sizes of the medial tibial component 130. The medial radii of curvature, thickness, size, specific placement, and/or other geometry of the medial tibial component may be further adjusted to facilitate specific ACL and PCL function by inducing different ranges of EFMs.

Figure 9B:
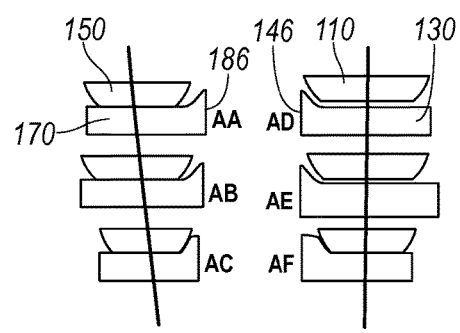
FIG. 9B is a view of frontal cross-sections of the medial and lateral tibial components, taken along the lines A-A through A-F of FIG. 9A, shown articulating with the medial and lateral femoral components, respectively.

As shown in FIGS. 9A and 9B, the most medial portion (relative to the midline of the tibia) of the medial tibial component 130 preferably includes a raised edge 146 that functions to constrain medial-lateral motion between the femur and the knee. The raised edge preferably slopes to a plateau with a curvature that complements the medial side of the medial femoral component no. As shown in FIGS. 9A and 9B, the raised edge 146 preferably increases in width as it approaches in an anterior direction and wraps around the anterior side of the medial tibial component 130.

The medial tibial component 130 is preferably made of a durable, wear-resistant, shock-absorbent biocompatible material, such as ultra-high molecular weight polyethylene. In an alternative version, the medial tibial component 130 is made of multiple materials such that different areas of the medial tibial component are optimized for different mechanical demands. As shown in FIG. 2, the anterior region 145' and posterior region 145 of the medial tibial component may be made of a material that is ideal for resisting fracture from impacts, and/or the central region 147 may be made of a material that is ideal for resisting adhesion and repeated abrasive wear. The medial tibial component 130 is preferably manufactured in a milling, casting, injection molding, sanding, polishing, and/or any other suitable manufacturing and finishing processes.

To achieve a natural medial EFM 107, the medial tibial component 130 is preferably implanted in a patient such that the anterior cruciate ligament (ACL) 103 and the posterior cruciate ligament (PCL) 101 function as they normally do in a healthy knee. In a healthy knee, as the knee reaches full leg extension there is anterior displacement and external rotation of the tibia (such as at onset of heel strike during walking). These motions load the ACL in tension, which allows the ACL to guide the anterior and external rotational motion of the tibia. In a simple leg extension test, an assessment of the tibial translation and external rotation as the leg extends may be performed to intraoperatively evaluate ACL function. Similarly, in a healthy knee, as the knee flexes to approximately 45 degrees, the PCL is in tension, which provides the posterior translation of the femur relative to the tibia during activities such as stair climbing. An iterative approach involving simulating heel strike and toe off with trial component sizes is preferably performed to select the appropriate size component and position the component, such that constraint of anterior-posterior motion of the component is similar to that in a healthy knee. An initial trial component size is preferably mounted on a fixture that permits anterior-posterior adjustment of the component, and the fixture is temporarily placed on the medial tibial plateau. Once the suitable size and anterior-posterior position of the trial component are found, the position is preferably marked and used to appropriately position a medial tibial component 130 for implantation. Adjustment of the medial tibial component may be performed at the same time as adjustment of the lateral tibial component 170, or may be performed iteratively in succession with adjustment of the lateral tibial component.

To adjust the posterior constraint of the medial tibial component 130, the size and/or anterior-posterior position of the component are preferably iteratively adjusted until ACL tension resists combined leg motions that simulate the natural knee conditions at onset of heel strike during walking. To adjust the anterior constraint of the medial tibial component, the size and/or anterior-posterior position are preferably iteratively adjusted until PCL tension resists combined leg motions that simulate the natural knee conditions at toe off during walking. When the tension of the ACL and/or the PCL resist these motions before the conflicting geometries of the medial femoral component 110 and the medial tibial component 130 resist these motions, the knee medial tibial component is appropriately positioned.

Figure 7B:
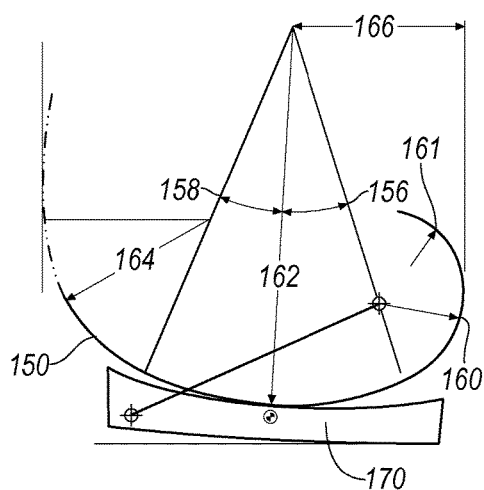

The lateral femoral component 150 of the knee replacement system functions to provide a bearing surface on the lateral condyle of the femur. As shown in FIG. 1, the lateral femoral component is preferably implantable on the lateral condyle on the distal end of the femur and preferably includes a lateral femoral articulating surface that 152 articulates with the lateral tibial articulating surface 172 of the lateral tibial component 170 throughout knee movement. The lateral femoral component 150 preferably covers and integrates with the lateral condyle located on the distal end of the femur. Except as noted below, the general geometry of the lateral femoral component 150 is preferably similar to that of the medial femoral component no. The specific local radii of curvature of the lateral femoral component 150 are designed for the lateral side of the knee, as shown in FIG. 7B. As shown in FIG. 7B, the sagittal profile of the lateral femoral articulating surface 152 is preferably defined by four lateral femoral arcuate portions (a superior, a posterior, a distal, and an anterior lateral femoral arcuate portion) and a scaling factor 166 measuring the offset from the posterior edge of the lateral condyle in the central sagittal plane of the lateral femoral component 150. The superior, posterior, distal, and anterior arcuate portions preferably have radii of curvature of a superior radius 161, a posterior radius 160, a distal radius 162, and an anterior radius 164, respectively, which are designed with considerations similar to those for the sagittal profile of the medial femoral component 110, but for various sizes of the lateral femoral component. The posterior, distal, and anterior radii of curvature of the lateral femoral component 150 may be different from that of the medial femoral component 110, for example, to accommodate anatomical differences between the medial and lateral sides of the knee. For example, the anterior and the distal lateral femoral radii of curvature 164 and 162 may be longer than the anterior and the distal medial femoral radii of curvature 124 and 122, respectively. As shown in FIG. 7B, the distal lateral femoral arcuate portion preferably sweeps the sum of a posterior angle 156 and an anterior angle 158. The lateral femoral component 150 is preferably made of the same material as the medial femoral component 110, and is preferably manufactured and implanted in a patient in a manner similar to that of the medial femoral component. However, the preparation of the lateral femoral condyle prior to implantation of the lateral femoral component is preferably coupled to the preparation of the medial femoral condyle, to preserve interdependence between components of the knee replacement system. The proper interdependence may be attained with, for example, the use of a jig, robot, instrumentation, or other guide.

Figure 8B:
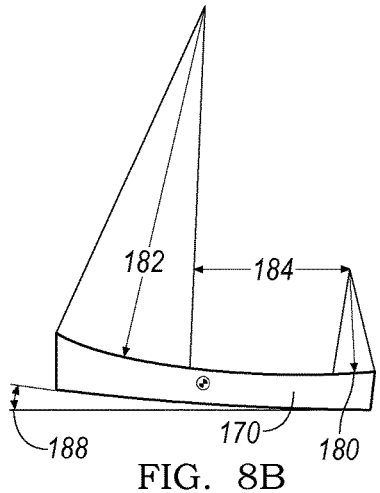

The lateral tibial component 170 functions to provide a bearing surface on the lateral tibial plateau of the tibia. As shown in FIG. 1, the lateral tibial component 170 is preferably implantable on the lateral tibial plateau on the proximal end of the tibia, and includes a lateral tibial articulating surface that preferably articulates with the lateral femoral component 150 throughout knee movement. The lateral tibial component 170 is preferably implanted on the proximal end of the tibia, by attaching to a lateral base plate that is fixated to a surgically-prepared proximal tibial plateau surface with biological fixation, bone cement, or another suitable fixative. However, the lateral tibial component 170 may alternatively be implanted directly to a surgically-prepared lateral tibial plateau surface, similar to the medial tibial component 130. Like the medial tibial component 130, the lateral tibial component 170 is preferably implanted such that the bottom surface (the distal surface) is at an angle 188 relative to the horizontal. The exact measurement of angle 188 preferably depends on the anatomy of the patient. The angle 188 is preferably introduced by implanting the lateral tibial component 130 in a sloped cut, but may alternatively be built into the lateral tibial component 130 to allow a horizontal, neutral cut. As shown in FIGS. 9A and 9B, the general geometry of the lateral tibial component 170 is preferably similar to that of the medial tibial component 130, including a medial raised edge 186, except that the specific local radii of curvature are designed for the lateral side of the knee, as shown in FIG. 8B. As shown in FIG. 8B, the sagittal profile of the lateral tibial component 170 is preferably defined by two lateral arcuate portions (a posterior and an anterior lateral tibial arcuate portions) and a scaling factor 184 measuring the lateral EFM. The posterior and anterior arcuate portions preferably have lateral radii of curvature 180 and 182, respectively. The posterior and anterior lateral tibial arcuate portions are preferably designed with considerations similar to those for the sagittal profile of the medial tibial component 130, but for various sizes of the lateral tibial component 170. The lateral tibial component is preferably made of the same material as the medial tibial component, and is preferably manufactured in a manner similar to that of the medial tibial component.

To achieve a natural lateral EFM, the lateral tibial component 170 is preferably implanted in a patient such that the PCL and the ACL function as they normally do in a healthy knee. In a healthy knee, deep leg flexion and internal rotation of the tibia (such as during squatting) is permitted by the PCL. In a healthy knee, nearly full leg extension with posterior displacement and internal rotation of the tibia (such as at onset of toe off during walking) loads the PCL in maximum tension, which allows the PCL to restrict posterior motion of the tibia. An iterative approach involving simulating squatting and toe off with trial component sizes is preferably performed to select the appropriate size component and position the component, such that constraint of anterior-posterior motion of the component is similar to that in a healthy knee. An initial trial component size is preferably mounted on a fixture that permits anterior-posterior adjustment of the component, and the fixture is temporarily placed on the medial tibial plateau. Once the suitable size and anterior-posterior position of the trial component are found, the position is preferably marked and used to appropriately position a medial tibial component 130 for implantation. Adjustment of the lateral tibial component may be performed at the same time as adjustment of the medial tibial component, or may be performed iteratively in succession with adjustment of the medial tibial component.

To adjust the posterior constraint of the lateral tibial component 170, the size and/or anterior-posterior position of the component are preferably iteratively adjusted until PCL tension permits leg motions that simulate the natural knee conditions during squatting. Adjustment of the anterior constraint of the lateral tibial component 170 is preferably identical to that of the medial tibial component 130. When slack of the PCL permits simulated squatting and the tension of the ACL resists simulated toe off before the conflicting geometries of the medial femoral component 110 and the medial tibial component 130 resist simulated toe off, the lateral tibial component 170 is appropriately positioned.

The patellar flange component 190 preferably functions to provide a contacting surface for the patella. As shown in FIG. 1, the patellar flange component 190 preferably attaches to the anterior distal portion of the femur, replacing or enhancing the anterior portion of the articular cartilage. The patellar flange 190 is preferably made of the same material as the medial and/or lateral femoral component, but may alternatively be made of any suitable material. The patellar flange component is preferably implanted on the femur with biological fixation, bone cement, or another suitable fixative in a manner similar to the medial and lateral femoral components. The patellar flange is preferably manufactured in a milling, casting, injection molding, sanding, polishing, and/or any suitable manufacturing and finishing processes, as known to one ordinarily skilled in the art of knee replacement systems.

Figure 18A:
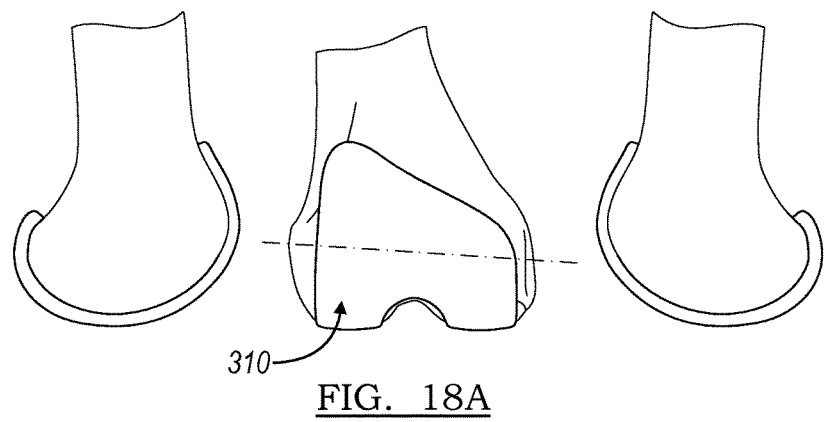
FIGS. 18A-18D are schematics of a full femoral component, a medial partial femoral component, a lateral partial femoral component, and a full tibial component, respectively, of a preferred embodiment.
Figures 18B, 18C:
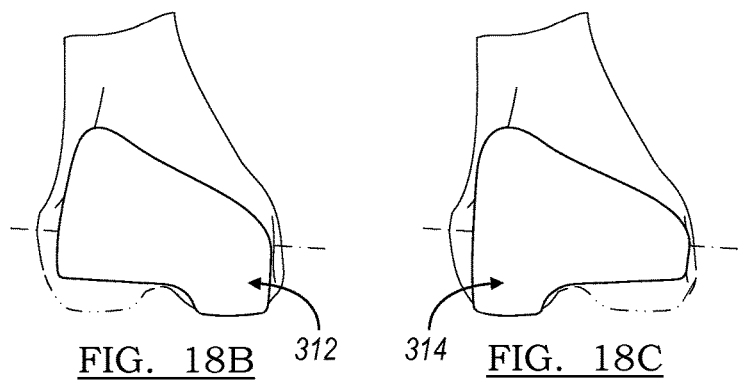

In a second preferred embodiment of the system, as shown in FIG. 18A, the system includes a full femoral component 310. The full femoral component 310 preferably includes the medial femoral component 110, the lateral femoral component 150, and the patellar flange component 190 integrated into one piece. In variations of this alternative embodiment, the system includes a medial partial femoral component 312 that includes the medial femoral component 110 and the patellar flange component 190 integrated into one piece (FIG. 18B), or a lateral partial femoral component 314 that includes the lateral femoral component 150 and the patellar flange component 190 integrated into one piece (FIG. 18C). Alternatively, the partial femoral components 312 and 314 may each include only a portion of the patellar flange component; for example, the medial partial femoral component 312 may include the medial half of the patellar flange component. The relative positions of the individual component portions within each of the full and partial femoral components are preferably substantially fixed, but may be slightly adjustable (for example, due to compliance in the material).

Figure 18D:
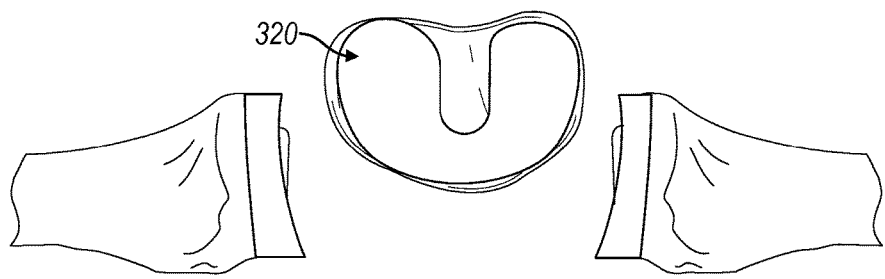

In a third alternative embodiment of the system, as shown in FIG. 18D, the system includes a full tibial component 320. The full tibial component 320 preferably includes the medial tibial component 130 and the lateral tibial component 170. As shown in FIG. 18D, the medial and lateral tibial components are preferably joined by a bridge 322 adapted to cross the anterior space between the medial and lateral tibial plateaus when the full tibial component 320 is implanted in a patient. However, the bridge 322 may additionally and/or alternatively join the medial and lateral tibial pieces at any location. The bridge 322 functions to secure the relative positions of the medial and tibial components. The bridge 322 is preferably slightly concave, curving distally towards the tibia when implanted, but may be flat or have any suitable profile. The bridge 322 is preferably one connection joining the medial and lateral tibial components, but may alternatively include multiple connections that join the medial and lateral tibial components, such as in a parallel, criss-cross, and/or web-like manner. However, the bridge 322 may be any suitable shape. Similar to the full and partial femoral components, the relative positions of the medial and tibial components in the full tibial component are preferably substantially fixed, but may be slightly adjustable (for example, due to compliance in the material).

In other alternative embodiments of the system, the system includes a patellar surface replacement. The patellar surface replacement functions to provide a replacement of the patellar surface that articulates with the femur. The patellar surface replacement is preferably made of a material similar to the medial and lateral tibial components, and implanted on the patella in a manner similar to the medial and lateral femoral components. The system may also include a patellar component to replace the entire patella and articulate with the femur.

One specific, exemplary embodiment of the system is shown in FIG. 11. The shown dimensions (which include various angles, radii of curvature, and other dimensions defining the geometry of the medial femoral component, medial tibial component, lateral femoral component, and lateral tibial component) that are designed for an average size Caucasian male.

2. Method of Supplying a Knee Replacement System for Implantation

As shown in FIG. 13, in a preferred embodiment, the method 400 of supplying a knee replacement system for implantation in a patient includes the steps of: providing a set of multiple medial femoral components, providing a set of multiple lateral femoral components, providing a set of multiple full femoral components, providing a set of multiple partial femoral components, providing a set of multiple medial tibial components, providing a set of multiple lateral tibial components, and providing a set of multiple full tibial components. The method may further include providing at least one patellar flange component, providing at least one patellar surface replacement component, and/or providing a patellar component. The medial femoral components, lateral femoral components, full and partial femoral components, medial tibial components, lateral tibial components, full tibial components, patellar flange components, patellar surface replacement components, and patellar components are preferably similar to those described above in Section 1.

In a first variation of the method, the method further includes the steps of selecting a medial femoral component from the set of multiple medial femoral components, and/or selecting a medial tibial component from the set of multiple medial tibial components. The selection may be based on consideration of at least one of multiple factors, including gender, patient height, patient weight, degree and type of knee degeneration, and/or any suitable factor. For instance, smaller components (femoral and tibial components scaled to a smaller scaling factor) may be more appropriate for a smaller patient. As another example, the steps of selecting a medial femoral component and selecting a medial tibial component may be performed for implantation of the knee system in a patient with degeneration on only the medial side of the knee.

In a second variation of the method, the method further includes the steps of selecting a lateral femoral component from the set of multiple lateral femoral components and a lateral tibial component from the set of multiple lateral tibial components. The second variation of the method is preferably similar to the first variation of the method, except the second variation of the method incorporates lateral side components of the knee system.

In a third variation of the method, the method further includes the step of selecting a full femoral component from the set of multiple full femoral components. Similarly, in a fourth variation of the method, the method further includes the step of selecting a full tibial component from the set of multiple full tibial components. The third and fourth variations are preferably similar to the first variation of the method, except the full femoral component incorporates both the medial and lateral side femoral components of the knee system, and the full tibial component incorporates both the medial and lateral side tibial components of the knee system.

In a fifth variation of the method, the method further includes the steps of selecting a medial partial femoral component or a lateral partial femoral component from the set of multiple partial femoral components. The fifth variation is preferably similar to the first variation of the method, except the fifth variation incorporates a medial partial femoral component (including a medial femoral component and at least a portion of the patellar flange component) or a lateral partial femoral component (including a lateral femoral component and at least a portion of the patellar flange component).

The method of supplying a knee replacement system includes every combination and permutation of the above described steps. As shown in FIG. 13, components of the knee replacement system may be implanted in different combinations in different "modes".

3. Method of Implanting a Knee Replacement System

Figure 14:
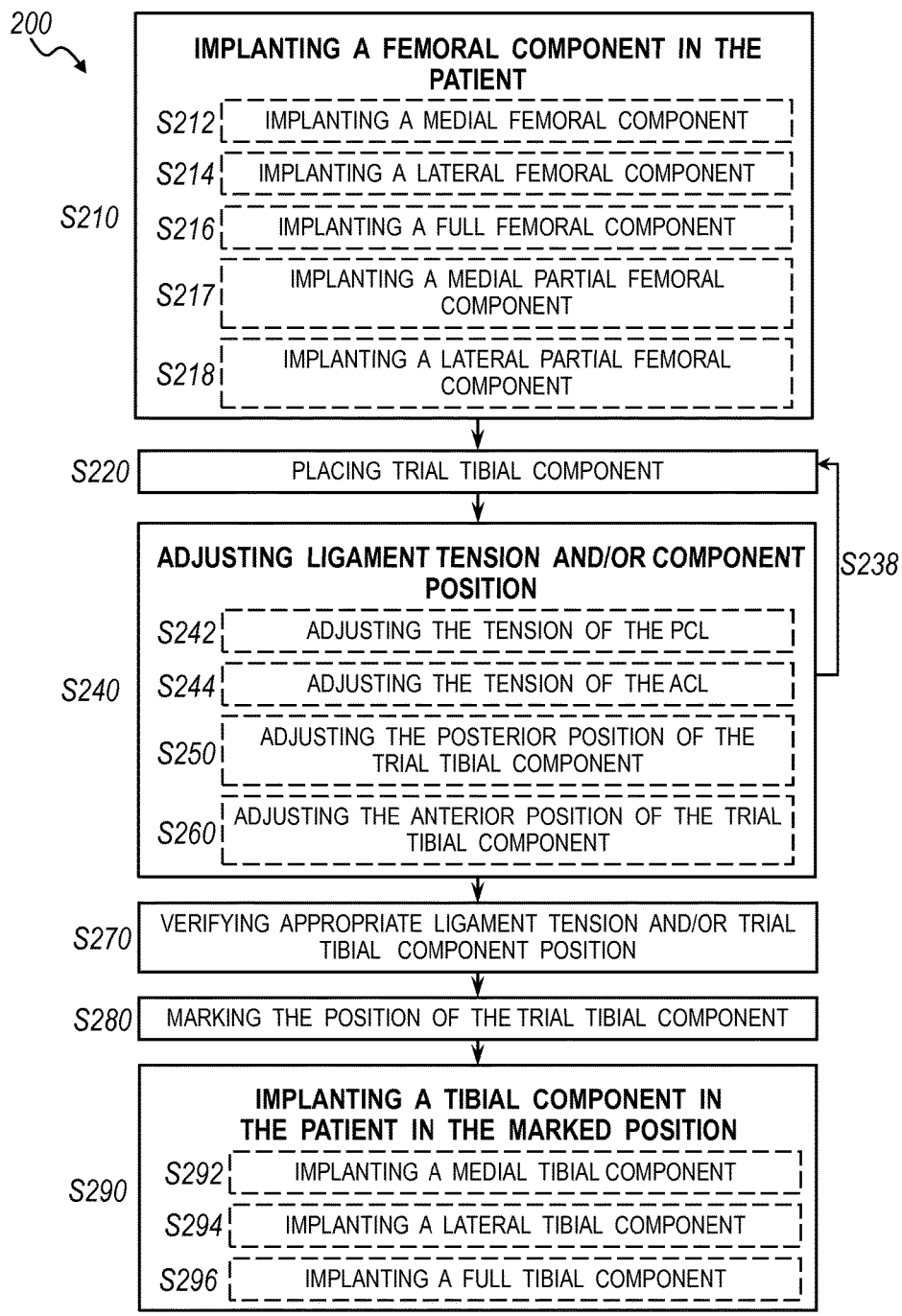
FIG. 14 is a flowchart of the preferred method for implanting the knee system of the preferred embodiment.

As shown in FIG. 14, the method 200 of implanting the knee replacement system in a leg of a patient includes the steps of implanting a femoral component onto a condyle of a femur in the leg S210, placing a trial tibial component on a tibial plateau of a tibia in the patient S220, adjusting at least one of tension of a cruciate ligament and position of the trial tibial component S24, verifying appropriate cruciate ligament tension and trial tibial component position S270, marking the position of the trial tibial component S28, and implanting a tibial component in the patient in the marked position S290.

The step of implanting a femoral component S210 is well known by one ordinarily skilled in the art. In a first variation, the step of implanting a femoral component includes implanting a medial femoral component S212. In a second variation, the step of implanting a femoral component includes implanting a lateral femoral component S214. In a third variation, the step of implanting a femoral component includes implanting a medial femoral component and implanting a lateral femoral component. Alternatively, the step of implanting a femoral component S210 includes implanting a full femoral component S216 that includes the medial and lateral femoral components, implanting a medial partial femoral component S217, and/or implanting a lateral partial femoral component S218. The medial femoral component preferably functions to bear load on the medial side of the knee and provide a bearing surface on the medial condyle, and is preferably adapted to cover and be integrated into the medial femoral condyle of the patient. Similarly, the lateral femoral component preferably functions to bear load on the lateral side of the knee and provide a bearing surface on the lateral condyle, and is preferably adapted to cover and be integrated into the lateral femoral condyle of the patient. The step of implanting a femoral component 210 may include selecting a femoral component size from group of available or supplied femoral components.

Figure 15:
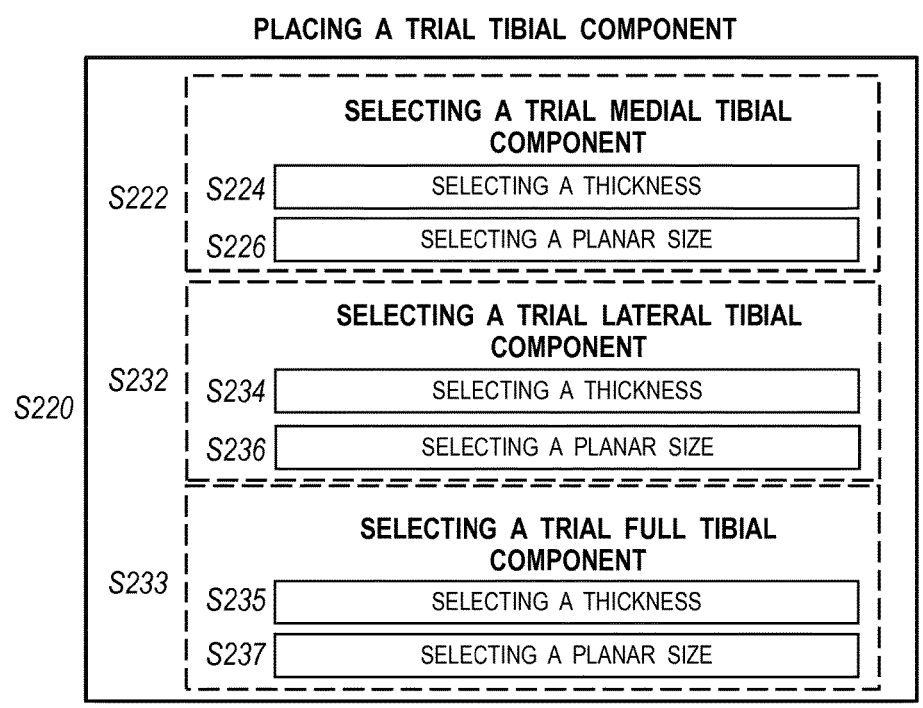
FIG. 15 is a flowchart detailing the step of placing a trial tibial component.

The step of placing a trial tibial component S220 preferably functions to establish a placeholder tibial component for testing suitability of fit. As shown in FIG. 15, in a first variation, the step of placing a trial tibial component S220 includes the step of selecting a trial medial tibial component S222. The step of selecting a trial medial tibial component S222 preferably includes selecting a thickness from a group of tibial component thicknesses S224, and selecting a size from a group of tibial component planar coverage sizes S226. As shown in FIG. 15, in a second variation, the step of selecting a trial tibial component S220 includes selecting a trial lateral tibial component S232. The step of selecting a trial lateral tibial component S232 preferably includes selecting a thickness from a group of tibial component thicknesses S234, and selecting a size from a group of tibial component sizes S236. In a third variation, the step of selecting a trial tibial component includes selecting a trial medial tibial component and selecting a trial lateral tibial component. The trial medial tibial component is preferably adapted to cover and be integrated into the medial tibial plateau of the patient. Similarly, the trial lateral tibial component is preferably adapted to cover and be integrated into the lateral tibial plateau of the patient. Alternatively, the step of placing a trial tibial component S220 may include placing a trial full tibial component S233 on both the medial and lateral tibial plateaus. The step of placing a trial full tibial component preferably includes selecting a thickness from a group of tibial component thicknesses S235 and selecting a size from a group of tibial component sizes S237. The step of placing a trial tibial component S220 may include the step of coupling the trial tibial component to a fixture that permits movement within a sagittal plane functions to prepare the trial tibial component for position adjustment. The step of coupling the trial tibal component to a fixture preferably includes positioning the fixture on a tibia of the patient relative to the femoral component such that the femoral component and the trial tibial component may articulate in knee motion. The trial tibial component is preferably removably coupled to the fixture. The fixture preferably allows movement of the trial tibial component in an anterior-posterior direction.

Step S240, which includes adjusting at least one of tension of a cruciate ligament and position of the trial tibial component, functions to obtain the correct fit of the knee replacement system in the patient. S240 preferably includes at least one of: adjusting tension of the posterior cruciate ligament S242, adjusting tension of the anterior cruciate ligament S244, adjusting the posterior position of the trial tibial component S250, and adjusting the anterior position of the trial tibial component S260. If the tension of the cruciate ligaments and the position of the trial tibial component do not need to be adjusted, steps S240 may be omitted.

The steps of adjusting tension of the posterior and anterior cruciate ligaments function to set the PCL and ACL to an appropriate amount of tension to facilitate a full range of motion in flexion and extension. In embodiments in which medial and lateral tibial components will be implanted in the patient, the PCL and ACL are preferably adjusted for both the medial and lateral sides simultaneously, since the medial and lateral envelopes of functional motion are not independent. An appropriately adjusted PCL preferably varies in tension throughout the knee range of motion, with tension beginning at 45 degrees of flexion and increasing with increasing flexion until maximum tension at 90 degrees flexion (using a reference of a straight extended leg as having 0 degrees of flexion). An appropriately adjusted ACL preferably has adequate tension to allow the leg to externally rotate at full extension, but without excessive tension that results in flexion contracture (inability to actively or passively fully extend the leg). The step of adjusting tension of the PCL S242 may include checking for excessive or insufficient PCL tension, reducing PCL tension to compensate for excessive PCL tension, and/or increasing PCL tension to compensate for insufficient PCL tension. Excessive or insufficient tension may be determined or tested by one or more of several ways. In a first variation, excessive tension is evident when the posterior femoral condyles migrate too far posteriorly with flexion, which may cause the posterior end of the trial tibial component to lift superiorly upwards. In a second variation, identifying the location of the tibiofemoral contact area and comparing to an ideal or desired location may indicate whether PCL tension is excessive, insufficient, or appropriate. For example, measuring displacement of the tibiofemoral contact area relative to reference marks created on the trial tibial component, using contact film, or other electronic or visual means of locating the tibiofemoral contact area may provide a quantitative determination of excessive or insufficient tension. In a third variation, excessive or insufficient tension may be determined by direct measure of tension in the PCL such as with an electronic instrument. Insufficient tension may be determined in a similar manner as excessive tension is determined. However, checking for excessive or insufficient tension may include any suitable step. The step of reducing tension in the PCL preferably includes increasing the flexion space between the femur and tibia, replacing the trial femoral component with a smaller size, preferably with a trial femoral component having a shorter anterior to posterior dimension (such as by 1-2 millimeters), although the trial tibial component may be replaced by another trial tibial component that is additionally and/or alternatively thinner, smaller in any suitable dimension, and/or any suitable shape to reduce the excessive tension in the PCL. Increasing tension in the PCL preferably includes decreasing the flexion space between the femur and tibia, such as by adding more material to the distal end of the femur, selecting a trial tibial component that is thicker in the posterior portion, or selecting a trial tibial component having a smaller radius of curvature (e.g., smaller posterior radius of curvature 140 or 180). However, reducing or increasing tension in the PCL may include any suitable step.

The step of adjusting tension of the ACL S244 may include checking for excessive or insufficient ACL tension, reducing ACL tension to compensate for excessive ACL tension, and/or increasing ACL tension to compensate for insufficient ACL tension. Checking for excessive or insufficient ACL tension may be one or more of several variations. In one variation, excessive ACL tension may be determined by identifying presence of flexion contracture where the flexion space between the femur and tibia is adequate and other collateral ligaments are balanced. In another variation, excessive or insufficient ACL tension may be determined by identifying that the leg is unable to passively externally rotate during full extension to a certain amount of external rotation. The amount of external rotation may be measured with an electronic instrument, visually, or any suitable means. Reducing ACL tension to compensate for excessive ACL tension may include selecting a trial tibial component that has a thinner anterior portion and/or has a larger radius of curvature (e.g., larger anterior radius of curvature 142 or 182). Increasing ACL tension to compensate for excessive ACL tension may include selecting a trial tibial component that has a thicker anterior portion and/or a smaller radius of curvature (e.g., smaller anterior radius of curvature 142 or 182).

Figure 16:
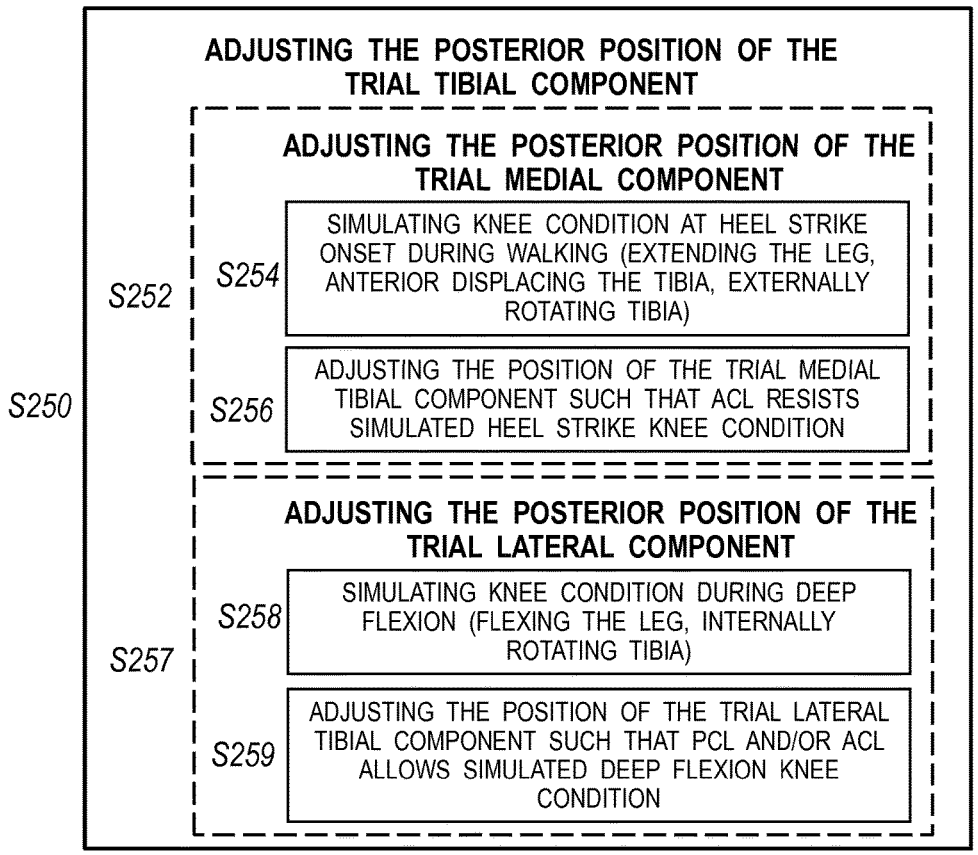
FIG. 16 is a flowchart detailing the step of adjusting the posterior position of the trial tibial component.

The step of adjusting the posterior position of the trial tibial component S250 functions to adjust the posterior constraint of the trial tibial component to enable a natural functional envelope of motion, using the natural function of cruciate ligaments in a healthy knee as a guide. As shown in FIG. 16, in a first variation, the step of adjusting the posterior position S250 includes adjusting the posterior position of the trial medial tibial component S252. As shown in FIG. 12A, the step of adjusting the posterior position of the trial medial tibial component S252 preferably includes simulating knee condition at onset of heel strike S254 and adjusting the position of the trial medial tibial component such that the ACL resists the simulated heel strike knee condition S256. The step of simulating knee condition at onset of heel strike S254 preferably includes extending the leg of the patient, anteriorly displacing the tibia relative to the femur, and externally rotating the tibia. Exercising the tibia in this manner functions to simulate knee conditions at onset of heel strike during walking, which is when the anterior cruciate ligament (ACL) is normally at maximum tension in a healthy knee. In a second variation, the step of adjusting the posterior position S250 includes adjusting the posterior position of the trial lateral tibial component S257. As shown in FIG. 12C, the step of adjusting the posterior position of the trial lateral tibial component S257 preferably includes simulating knee condition during deep flexion S258 and adjusting the position of the trial lateral tibial component such that the PCL and/or ACL allows simulated deep flexion knee condition S259. The step of simulating knee condition during deep flexion S258 preferably includes flexing the leg and internally rotating the tibia. In the step of simulating knee condition during deep flexion, the leg is preferably flexed to approximately 145 degrees (relative to a straight-leg angle of zero degrees), but may alternatively be flexed to any suitable angle. Exercising the tibia in this manner functions to simulate knee conditions during squatting, that is when the posterior cruciate ligament (PCL) is normally slack enough to permit deep flexion. In a third variation, the step of adjusting the posterior position S250 includes adjusting the posterior position of the trial medial tibial component and adjusting the posterior position of the trial lateral tibial component, in which the steps of adjusting the posterior positions of the trial medial tibial component and the trial lateral tibial component are preferably identical to those of the first and second variations, respectively. If the adjusting steps as described are not possible, the method is preferably repeated, beginning with the step of selecting a trial tibial component.

Figure 17:
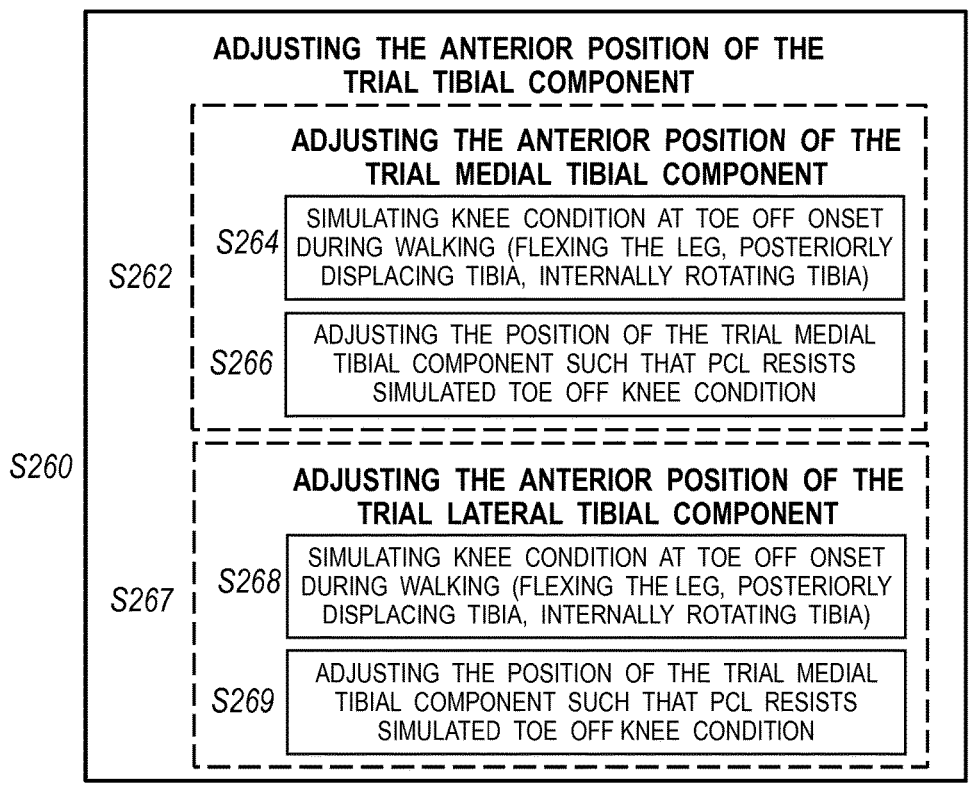
FIG. 17 is a flowchart detailing the step of adjusting the anterior position of the trial tibial component.

The step of adjusting the anterior position of the trial tibial component S260 functions to adjust the anterior constraint of the trial tibial component to enable a natural functional envelope of motion, using the natural function of cruciate ligaments in a healthy knee as a guide. As shown in FIGS. 12B and 17, in a first variation, the step of adjusting the anterior position S260 includes adjusting the anterior position of the trial medial tibial component S262. The step of adjusting the anterior position of the trial medial tibial component S262 preferably includes simulating knee condition during onset of toe off during walking S264 and adjusting the position of the trial medial tibial component such that the PCL resists the simulated toe off knee condition S266. The step of simulating knee condition at toe off onset S264 preferably includes flexing the leg, posteriorly displacing the tibia relative to the femur, and internally rotating the tibia. Exercising the tibia in this manner functions to simulate knee conditions at onset of toe off during walking, which is when the PCL is normally at a maximum tension in a healthy knee. In a second variation, the step of adjusting the anterior position S260 includes adjusting the anterior position of the trial lateral tibial component S267. The step of adjusting the anterior position of the trial lateral tibial component S267 preferably includes simulating knee condition during onset of toe off during walking S268 and adjusting the position of the trial lateral tibial component such that the PCL resists the simulated toe off knee condition S269. The step of simulating knee condition S268 and adjusting the position of the trial lateral tibial component S269 are preferably similar to steps S264 and S266, respectively, of adjusting the anterior position of the trial medial tibial component S262. In a third variation, the step of adjusting the anterior position includes adjusting the anterior position of the trial medial tibial component and adjusting the anterior position of the trial lateral tibial component, in which the steps of adjusting the anterior positions of the trial medial tibial component and the trial lateral tibial component are preferably identical to those of the first and second variations, respectively.

Step S270, which includes verifying appropriate cruciate ligament tension and trial tibial component position, preferably includes steps similar to those for checking for excessive or insufficient tension of the PCL, checking for excessive or insufficient tension of the ACL, simulating heel strike onset during adjustment of the posterior position of the trial medial tibial component, and simulating the knee condition in deep flexion during adjustment of the anterior position of the trial lateral tibial component.

The step of marking the position of the trial tibial component S280 functions to record the optimum position of the trial tibial component based on the adjustments in position of the trial tibial component. The step of marking the position may be performed with biocompatible ink, a photograph, an etching in tissue, or any suitable process. Alternatively, the position may be recorded with a photograph or other recording equipment.

The step of implanting a tibial component in the patient S290 based on the marked position is preferably similar to the step of implanting a femoral component in the patient. In a first variation, the step of implanting a tibial component S290 includes implanting a medial tibial component on the medial tibial plateau of the leg S292. In a second variation, the step of implanting a tibial component S290 includes implanting a lateral tibial component on the lateral tibial plateau of the leg S294. In a third variation, the step of implanting a tibial component includes implanting a full tibial component S296 that includes a medial tibial portion and a lateral tibial portion. In a fourth variation, the step of implanting a tibial component includes implanting a medial tibial component and implanting a lateral tibial component. The medial tibial component preferably functions to bear load on the medial side of the knee, and is preferably adapted to cover and be integrated into the medial tibial plateau of the patient. Similarly, the lateral tibial component preferably functions to bear load on the lateral side of the knee, and is preferably adapted to cover and be integrated into the lateral tibial plateau of the patient.

The method may further include the step of repeating at least a portion of the method S238 if the performing at least one of the steps of adjusting the tension of the PCL S282, adjusting the tension of the ACL S284, adjusting the posterior position S250 and adjusting the anterior position S260 are prevented by the trial tibial component size. For example, the steps of placing a trial tibial component S220 (including selecting a trial tibial component), adjusting the posterior position S250, and adjusting the anterior position S260 may be repeated until both adjusting steps S250 and S260 are successful.

Alternative versions of the method include the steps of adjusting the posterior position and adjusting the anterior position performed in any combination and/or permutation, or simultaneously. As an example, adjusting the anterior position may be performed before adjusting the posterior position. As another example, the steps of adjusting the posterior position and adjusting the anterior position may be performed simultaneously, by performing their substeps the following order: adjusting the posterior position of the trial medial tibial component, adjusting the anterior position of the trial medial tibial component, adjusting the posterior position of the trial lateral tibial component, and adjusting the anterior position of the trial medial tibial component.

As a person skilled in the art will recognize from the previous detailed description and from the figures and claims, modifications and changes can be made to the preferred embodiments of the invention without departing from the scope of this invention defined in the following claims.

We claim:

1. A knee replacement system for enabling natural knee movement in a leg with a femur having medial and lateral condyles and a tibia having medial and lateral tibial plateaus in a patient, comprising:
a femoral component including:
a medial femoral portion, implantable on the medial condyle and having a medial femoral articulating surface, wherein the medial femoral articulating surface has a medial femoral sagittal plane profile including first superior, first posterior, first distal, and first anterior femoral arcuate portions scaled by a first femoral scaling factor wherein the first distal femoral arcuate portion sweeps a greater number of degrees than each of the first posterior femoral arcuate portion and the first anterior femoral arcuate portion, wherein the first superior, first posterior, first distal, and first anterior femoral arcuate portions have first superior, first posterior, first distal, and first anterior femoral radii of curvature, respectively, wherein the first distal femoral radius of curvature is longer than each of the first posterior and first anterior femoral radii of curvature, and wherein the first femoral scaling factor comprises a measure of the offset from a posterior edge of the medial condyle in a central sagittal plane to the first distal femoral radius of curvature which extends to intersect a point of initial articular contact between the medial femoral portion and a medial tibial portion of a tibial component; and
a lateral femoral portion, implantable on the lateral condyle and having a lateral femoral articulating surface, wherein the lateral femoral articulating surface has a lateral femoral sagittal plane profile including second superior, second posterior, second distal, and second anterior femoral arcuate portions scaled by a second femoral scaling factor wherein the first distal femoral arcuate portion sweeps a greater number of degrees than the second distal femoral arcuate portion, wherein the second distal femoral arcuate portion has a second distal femoral radius of curvature, wherein the second distal femoral radius of curvature is longer than the first distal femoral radius of curvature, and wherein the second femoral scaling factor comprises a measure of the offset from a posterior edge of the lateral condyle in a central sagittal plane to the second distal femoral radius of curvature which extends to intersect a point of initial articular contact between the lateral femoral portion and a lateral tibial portion of the tibial component; and
the tibial component including at least one of:
the medial tibial portion, implantable on the medial tibial plateau and having a medial tibial articulating surface that articulates with the medial femoral articulating surface, wherein the medial tibial articulating surface includes a first plateau and a first raised medial edge that increases in width in an anterior direction and curves distally to the first plateau; and
the lateral tibial portion, implantable on the lateral tibial plateau and having a lateral tibial articulating surface that articulates with the lateral femoral articulating surface, wherein the lateral tibial articulating surface includes a second plateau and a second raised medial edge that increases in width in the anterior direction and curves distally to the second plateau.

2. The system of claim 1, wherein the tibial component is a full tibial component that includes both a medial tibial portion and a lateral tibial portion.

3. The system of claim 1, further comprising a patellar flange component, monolithic with the femoral component and implantable on an anterior distal portion of the femur, that is adapted to provide a contacting surface for a patella of the leg.

4. The system of claim 1, further comprising a patellar component implantable to replace the patella of the leg, that articulates with the patellar flange component.

5. The system of claim 1, wherein the first superior, first posterior, first distal, and first anterior femoral arcuate portions have superior, posterior, distal and anterior femoral arc centers, respectively; wherein the superior, posterior, distal, and anterior femoral arc centers are distinct points in the medial femoral sagittal plane.

6. The system of claim 1, wherein the medial tibial articulating surface has a medial tibial sagittal plane profile including:
a first posterior tibial arcuate portion located posterior to the first plateau, that has a posterior tibial arc center; and
a first anterior tibial arcuate portion, located anterior to the first plateau, that has an anterior tibial arc center;

wherein the posterior tibial arc center and the anterior tibial arc center are distinct points in the medial tibial sagittal plane.

7. The system of claim 1, wherein the lateral tibial articulating surface has a lateral tibial sagittal plane profile including a second posterior tibial arcuate portion, located posterior to the second plateau and having a posterior tibial radius of curvature, and a second anterior tibial arcuate portion located anterior to the second plateau and having an anterior tibial radius of curvature; wherein the anterior tibial radius of curvature is greater than the posterior tibial radius of curvature.

8. The system of claim 1, wherein the medial femoral portion is one of a plurality of medial femoral portions of different sizes, wherein relative lengths of the first superior, first posterior, first distal, and first anterior femoral radii of curvature are constant over the plurality of medial femoral portions.

9. The system of claim 8, wherein each one of the plurality of medial femoral portions is sized to the first femoral scaling factor, the first femoral scaling factor is the same dimension for each one of the plurality of the medial femoral portions.

10. The system of claim 1, wherein the first femoral scaling factor measures an offset from a posterior edge of the medial femoral portion in the medial femoral sagittal plane profile; and
wherein the second femoral scaling factor measures an offset from a posterior edge of the lateral femoral portion in the lateral femoral sagittal plane profile.

11. A knee replacement system for enabling natural knee movement in a leg with a femur having medial and lateral condyles and a tibia having medial and lateral tibial plateaus, the system comprising:
a plurality of medial femoral components each implantable on the medial condyle and each having a medial femoral articulating surface with a medial femoral sagittal plane profile including:
a first superior, a first posterior, a first distal, and a first anterior femoral arcuate portion each scaled by a first femoral scaling factor and each having a first superior, a first posterior, a first distal, and a first anterior femoral radii of curvature respectively with relative lengths that are constant for each one of the plurality of medial femoral components, and wherein the first femoral scaling factor comprises a measure of the offset from a posterior edge of the medial condyle in a central sagittal plane to the first distal femoral radius of curvature which extends to intersect a point of initial articular contact between the medial femoral articulating surface and a medial tibial component;
wherein the first distal femoral radius of curvature is longer than each of the first posterior and first anterior femoral radii of curvature; and
wherein the first distal femoral arcuate portion sweeps a greater number of degrees than each of the first posterior femoral arcuate portion and the first anterior femoral arcuate portion;
a plurality of lateral femoral components each implantable on the lateral condyle and each having a lateral femoral articulating surface with a lateral femoral sagittal plane profile including:
a second superior, a second posterior, a second distal, and a second anterior femoral arcuate portion each scaled by a second femoral scaling factor and each having a second superior, a second posterior, a second distal, and a second anterior femoral radii of curvature respectively with relative lengths that are constant for each one of the plurality of lateral femoral components, and wherein the second femoral scaling factor comprises a measure of the offset from a posterior edge of the lateral condyle in a central sagittal plane to the second distal femoral radius of curvature which extends to intersect a point of initial articular contact between the lateral femoral articulating surface and a lateral tibial component;
wherein the second distal femoral radius of curvature is longer than each of the second posterior and second anterior femoral radii of curvature; and
wherein the second distal femoral arcuate portion sweeps a greater number of degrees than each of the second posterior femoral arcuate portion and the second anterior femoral arcuate portion;
wherein the first distal femoral arcuate portion sweeps a greater number of degrees than the second distal femoral arcuate portion; and
wherein the second distal femoral radius of curvature is longer than the first distal femoral radius of curvature.

12. The system of claim 11, further comprising:
a plurality of medial tibial components implantable on the medial tibial plateau each having a medial tibial articulating surface that is configured to articulate with the medial femoral articulating surface, each medial tibial articulating surface includes a first plateau and a first raised medial edge that increases in width in an anterior direction and curves distally to the first plateau; and
a plurality of lateral tibial components implantable on the lateral tibial plateau each having a lateral tibial articulating surface that is configured to articulate with the lateral femoral articulating surface, each lateral tibial articulating surface includes a second plateau and a second raised medial edge that increases in width in the anterior direction and curves distally to the second plateau.

13. The system of claim 11, wherein the first scaling factor is the same dimension for each one of the plurality of medial femoral components and the second scaling factor is the same dimension for each one of the plurality of lateral femoral components.

14. The system of claim 11, wherein the first femoral scaling factor measures an offset from a posterior edge of the medial femoral portions in the medial femoral sagittal plane profile and is the same dimension for each one of the plurality of medial femoral components.

15. The system of claim 11, wherein the second femoral scaling factor measures an offset from a posterior edge of the lateral femoral portions in the lateral femoral sagittal plane profile and is the same dimension for each one of the plurality of lateral femoral components.

16. The system of claim 11, wherein the first femoral scaling factor measures an offset from a posterior edge of the medial femoral portions in the medial femoral sagittal plane profile; and
wherein the second femoral scaling factor measures an offset from a posterior edge of the lateral femoral portions in the lateral femoral sagittal plane profile.

17. The system of claim 11, wherein the first femoral scaling factor of at least one of the plurality of medial femoral components is the same as the second femoral scaling factor of at least one of the plurality of lateral femoral components.

18. The system of claim 11, further comprising a plurality of medial tibial components configured to be implanted on the medial tibial plateau and each having a medial tibial articulating surface that articulates with the medial femoral articulating surface;
  wherein the medial tibial articulating surface includes a first plateau and a first raised medial edge that increases in width in an anterior direction and curves distally to the first plateau.

19. The system of claim 18, further comprising a plurality of lateral tibial components configured to be implanted on the lateral tibial plateau and having a lateral tibial articulating surface that articulates with the lateral femoral articulating surface;
  wherein the lateral tibial articulating surface includes a second plateau and a second raised medial edge that increases in width in the anterior direction and curves distally to the second plateau.

20. The system of claim 11, wherein each one of the plurality of medial femoral components is monolithic with one of the plurality of lateral femoral components.

21. The system of claim 11, further comprising a plurality of patellar flange components each monolithic with one of the plurality of medial femoral components and one of the plurality of lateral femoral components.

22. A knee replacement system for enabling natural knee movement in a leg with a femur having medial and lateral condyles and a tibia having medial and lateral tibial plateaus, the system comprising:
  a plurality of medial femoral components each implantable on the medial condyle and each having a medial femoral articulating surface with a medial femoral sagittal plane profile including:
    a first superior, a first posterior, a first distal, and a first anterior femoral arcuate portion each scaled by a first femoral scaling factor and each having a first superior, a first posterior, a first distal, and a first anterior femoral radii of curvature respectively with relative lengths that are constant for each one of the plurality of medial femoral components;
    wherein the first distal femoral radius of curvature is longer than each of the first posterior and first anterior femoral radii of curvature; and
    wherein the first distal femoral arcuate portion sweeps a greater number of degrees than each of the first posterior femoral arcuate portion and the first anterior femoral arcuate portion;
  a plurality of lateral femoral components each implantable on the lateral condyle and each having a lateral femoral articulating surface with a lateral femoral sagittal plane profile including:
    a second superior, a second posterior, a second distal, and a second anterior femoral arcuate portion each scaled by a second femoral scaling factor and each having a second superior, a second posterior, a second distal, and a second anterior femoral radii of curvature respectively with relative lengths that are constant for each one of the plurality of lateral femoral components;
    wherein the second distal femoral radius of curvature is longer than each of the second posterior and the second anterior femoral radii of curvature; and
    wherein the second distal femoral arcuate portion sweeps a greater number of degrees than each of the second posterior femoral arcuate portion and the second anterior femoral arcuate portion;
  wherein:
    the first scaling factor comprises a measure of the offset from a posterior edge of the medial condyle in a central sagittal plane to the first distal femoral radius of curvature which extends to intersect a point of initial articular contact between the medial femoral articulating surface and a medial tibial component;
    the second scaling factor comprises a measure of the offset from a posterior edge of the lateral condyle in a central sagittal plane to the second distal femoral radius of curvature which extends to intersect a point of initial articular contact between the lateral femoral articulating surface and a lateral tibial component;
    the first scaling factor is the same dimension for each one of the plurality of medial femoral components;
    the second scaling factor is the same dimension for each one of the plurality of lateral femoral components;
    the first distal femoral arcuate portion sweeps a greater number of degrees than the second distal femoral arcuate portion; and
    the second distal femoral radius of curvature is longer than the first distal femoral radius of curvature.

23. The system of claim 22, wherein the first posterior radius of curvature of at least one of the plurality of medial femoral components is the same as the second posterior radius of curvature of at least one of the plurality of monolithic lateral femoral components.

24. The system of claim 22, wherein the first scaling factor of at least one of the plurality of medial femoral components is the same dimension as the second scaling factor of at least one of the plurality of lateral femoral components.

25. The system of claim 22, further comprising a plurality of patellar flange components each monolithic with one of the plurality of medial femoral components and one of the plurality of lateral femoral components.

26. The system of claim 22, further comprising a plurality of medial tibial components configured to be implanted on the medial tibial plateau and each having a medial tibial articulating surface that articulates with the medial femoral articulating surface;
  wherein the medial tibial articulating surface includes a first plateau and a first raised medial edge that increases in width in an anterior direction and curves distally to the first plateau.

27. The system of claim 26, further comprising a plurality of lateral tibial components configured to be implanted on the lateral tibial plateau and having a lateral tibial articulating surface that articulates with the lateral femoral articulating surface;
  wherein the lateral tibial articulating surface includes a second plateau and a second raised medial edge that increases in width in the anterior direction and curves distally to the second plateau.

28. A knee replacement system for enabling natural knee movement in a leg with a femur having medial and lateral condyles and a tibia having medial and lateral tibial plateaus, the system comprising:
  a plurality of medial femoral components each having a medial femoral articulating surface scaled to a distinct medial femoral scaling factor;
  a plurality of lateral femoral components each having a lateral femoral articulating surface scaled to a distinct lateral femoral scaling factor;
  a plurality of medial tibial components each having a medial tibial articulating surface configured to articulate with the medial femoral articulating surface and scaled to a distinct medial tibial scaling factor; and a plurality of lateral tibial components each having a lateral tibial articulating surface configured to articulate with the lateral femoral articulating surface and scaled to a distinct lateral tibial scaling factor;

wherein:

the distinct medial femoral scaling factor comprises a measure of the offset from a posterior edge of the medial condyle in a central sagittal plane to a first distal femoral radius of curvature which extends to intersect a point of initial articular contact between the medial femoral articulating surface and the medial tibial articulating surface; and the distinct lateral femoral scaling factor comprises a measure of the offset from a posterior edge of the lateral condyle in a central sagittal plane to a second distal femoral radius of curvature which extends to intersect a point of initial articular contact between the lateral femoral articulating surface and the lateral tibial articulating surface.

* * * * *